US006399759B1

(12) United States Patent
Travis et al.

(10) Patent No.: US 6,399,759 B1
(45) Date of Patent: Jun. 4, 2002

(54) ANT PROTEASES AND METHODS OF INHIBITION

(75) Inventors: James Travis, Athens, GA (US); S. Troy Whitworth, Apex, NC (US); Murray S. Blum, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/578,303

(22) Filed: May 25, 2000

Related U.S. Application Data

(60) Provisional application No. 60/136,331, filed on May 27, 1999.

(51) Int. Cl.⁷ .............................................. C07H 21/04
(52) U.S. Cl. ........................ 536/23.2; 435/195; 435/218
(58) Field of Search .......................... 536/23.2; 435/195, 435/218

(56) References Cited

U.S. PATENT DOCUMENTS

| | | | |
|---|---|---|---|
| 4,341,761 A | 7/1982 | Ganfield et al. | 424/85.6 |
| 4,399,121 A | 8/1983 | Albarella et al. | 530/363 |
| 4,427,783 A | 1/1984 | Newman et al. | 436/542 |
| 4,444,887 A | 4/1984 | Hoffmann | 435/373 |
| 4,466,917 A | 8/1984 | Nussenzweig et al. | 530/350 |
| 4,472,500 A | 9/1984 | Milstein et al. | 435/70.21 |
| 4,491,632 A | 1/1985 | Wands et al. | 435/339 |
| 5,746,021 A | 5/1998 | Green | 43/131 |
| 6,077,687 A * | 6/2000 | Grieve et al. | 435/69.1 |

FOREIGN PATENT DOCUMENTS

| WO | WO9611706 | * | 4/1996 |
|---|---|---|---|

OTHER PUBLICATIONS

Altschul et al., "Gapped BLAST and PSI–BLAST: a new generation of protein database search programs," *Nuc. Acids Res.*, 25(17):3389–3402 (1997).
Ausubel et al., eds., *Current Protocols in Molecular Biology*, John Wiley & Sons, Inc. United States, Title page, publication page and table of contents only, 12 pages (1994).
BasicBLAST, www.ncbi.nlm.nih.gov/blast/blast.cgi, 2 pages (available on–line as of May 27, 1999).
BLAST 2 Sequences, www.ncbi.nlm.nih.gov/gorf/bl2.html, 1 page (available on–line as of May 27, 1999).
Bleasby et al., "Construction of validated, non–resundant composite protein sequence databases," *Prot. Eng.*, 3(3):153–159 (1990).
Bode et al., "X–ray crystal structure of the complex of human leukocyte elastase (PMN elastase) and the third domain of the turkey ovomucoid inhibitor," *EMBO J.*, 5(10):25453–2458 (1986).
Bode et al., "Human Leukocyte and Porcine Pancreatic Elastase: X–ray Crystal Structures, Mechanism, Substrate Specificity, and Mechanism–Based Inhibitors," *Biochem.*, 28 (5):1951–1963 (1989).

Brosius et al., "Gene Organization ad Primary Structure of a Ribosomal RNA Operon from *Escherichia coli*," *J. Mol. Biol.*, 148:107–127 (1981).
Emi et al., "Cloning, characterization and nucleotide sequences of two cDNAs encoding human pancreatic trypsinogens," *Gene*, 41:305–310 (1986).
Farley et al., "The Human Neutrophil Elastase Gene," *Biol. Chem. Hoppe–Seyler*, 370:737–744 (1989).
Feinberg et al., "A Technique for Radiolabeling DNA Restriction Endonuclease Fragments to High Specific Activity," *Anal. Biochem.*, 132(1):6–13 (1983).
Glišin et al., "Ribonucleic Acid Isolated by Cesium Chloride Centrifugation," Biochem., 13(12):2633–2637 (1974).
Gubler et al., "A simple and very efficient method for generating cDNA libraries," *Gene*, 25:263–269 (1983).
Hämmerling et al., eds *Monoclonal Antibodies and T–Cell Hybridomas, Perspectives and technical advances*, Elservier/North–Holland Biomedical Press, Amerstdam, Title page, publication page, and table of contents only, 8 pages (1981).
Hölldobler et al., *The Ants*, Harvard University Press, Cambridge, Title page, publication page, and table of contents only, 8 pages (1990).
Jany et al., "The amino acid sequences around the reactive serine and histidine residues of the chymotrypsin–like protease from the hornet, *Vespa orientalis*," *Biochim. Biophys. Acta*, 668:197–200 (1981).
Jany et al., "Amino acid sequence of an insect chymotrypsin from the larvae of the hornet, *Vespa orientalis*," *Biochem. Biophys. Res. Comm.*, 110(1):1–7 (1983).
Jones et al., "Leupeptin, a protease inhibitor, blocks insemination–induced flight muscle histolysis in the fire ant *Solenopsis*," *Tissue Cell*, 17(1):111–116 (1985).
Kalhok et al., "Isolation, sequencing and characterization of two cDNA clones coding for trypsin–like enzymes from the midgut of *Aedes aegypti*," *Insect Mol. Biol.*, 2:71–79 (1993).
Kan et al., "Molecular mechanisms for the conversion of zymogens to active proteolytic enzymes," *Protein Sci.*, 7(4):815–836 (1998).
Kennett et al., eds *Monoclonal Antibodies Hybridomas: A New Dimension in Biological Analyses*, Plenum Press, New York, Title page, publication page, and table of contents only, 10 pages (1980).

(List continued on next page.)

*Primary Examiner*—Elizabeth Slobodyansky
(74) *Attorney, Agent, or Firm*—Mueting, Raasch & Gebhardt, P.A.

(57) ABSTRACT

The present invention provides polypeptides, including chymotrypsin-like polypeptides and elastase-like polypeptides, having amidolytic acitivity for cleavage of a peptide bond present in a target polypeptide. The polypeptides can be isolated from ants, including *S. invicta* larvae. Isolated nucleic acid fragments encoding isolated polypeptides are also provided, as are methods of developing and using inhibitors of chymotrypsin-like polypeptides and elastase-like polypeptides.

3 Claims, 4 Drawing Sheets

OTHER PUBLICATIONS

Matsudaira, "Sequences from Picomole Quantities of Proteins Electroblotted onto Polyvinylidene Difluroide Membranes," *J. Biol. Chem.*, 262(21):10035–10038 (1987).

Mayer et al., *Immunochemical Methods in Cell and Molecular Biology*, Academic Press Ltd., San Diego, Title page, publication page and table of contents only, 9 pages (1987).

Mikeš et al., "Covalent structure of bovine trypsinogen, the position of the remaining amides," *Biochem. Biophys. Res. Comm.*, 24(3):346–352 (1966).

Petralia et al., "Feeding in the Larvae of the Imported Fire Ant, *Solenopsis invicta*: Behavior and Morphological Adaptations," *Ann. Entomol. Soc. Am.*, 71(4):643–648 (1978).

Petralia et al., "Developmental Morphology of Larvae and Eggs of the Imported Fire Ant, *Solenopsis invicta*," *Ann. Entomol. Soc. Am.*, 72:472–484 (1979).

Petralia et al., "The Labial Gland System of Larvae of the Imported Fire Ant, *Solenopsis invicta* Buren," *Cell Tissue Res.*, 206:145–156 (1980).

Rose–John et al., "Molecular cloning of mouse protein kinase C (PKC) cDNA from Swiss 3T3 fibroblasts,"*Gene*, 74:465–471 (1988).

Sambrook et al., Molecular Cloning, a Laboratory Manual, second edition, Cold Spring Harbor Laboratory Press, Cold Spring Harbor, NY, Title page, publication page, table of contents and chapter 11, pp. 11.1–11.61, 91 pages (1989).

Schägger et al., "Tricine–Sodium Dodecyl Sulfate–Polyacrylamide Gel Electrophoresis for the Separation of Proteins in the Range from 1 to 100 kDa," *Anal. Biochem.*, 166:368–379 (1987).

Scherrer et al., "Sedimentation characteristics of rapidly labelled RNA form HELA cells," *Biochem. Biophys. Res. Comm.*, 7(6):486–490 (1962).

Schreier et al., *Hybridoma Techniques*, Cold Spring Harbor Laboratory, Cold Spring Harbor, NY, Title page, publication page and table of contents only, 4 pages (1980).

Sorenson et al., "The influence of oral secretins from larvae on levels of proteinases in colony members of *Solenopsis invicta* buren (Hymemoptera: Formicidae)," *J. Insect Physiol.*, 29(2):163–168 (1983).

Stradling, "Chapter 5. Food and feeding habits of ants," *Production ecology of ants and termites*, Brian, ed., Cambridge University Press, Great Britain, Title page, publication page, and pp. 81–106 (1978).

Tatusova et al., "BLAST 2 Sequences, a new tool for comparing protein and nucleotide sequences," *FEMS Microbiol. Lett.*, 174:247–250 (1999).

Travis et al., "Proteinases from pollen and pests," *Acta Biochim. Polonica*, 43(3):411–417 (1996).

Ullrich et al., "Rat Insulin Genes: Construction of Plasmids Containing the Coding Sequences," *Science*, 196(4296):1313–1319 (1977).

Whitworth et al., "Proteolytic Enzymes form Larvae of the Fire Ant, *Selenopsis invicta*," *J. Biol. Chem.*, 273(23):14430–14434 (available on–line May 29, 1998; mailed Jun. 1, 1998).

Whitworth et al., "Molecular cloning of Soli E2:an elastase–like serine proteinase from the imported red fire ant (*Solenopsis invicta*)," *Insect Biochem. Mol. Biol.*, 29(8):249–254 (Mar., 1999).

* cited by examiner

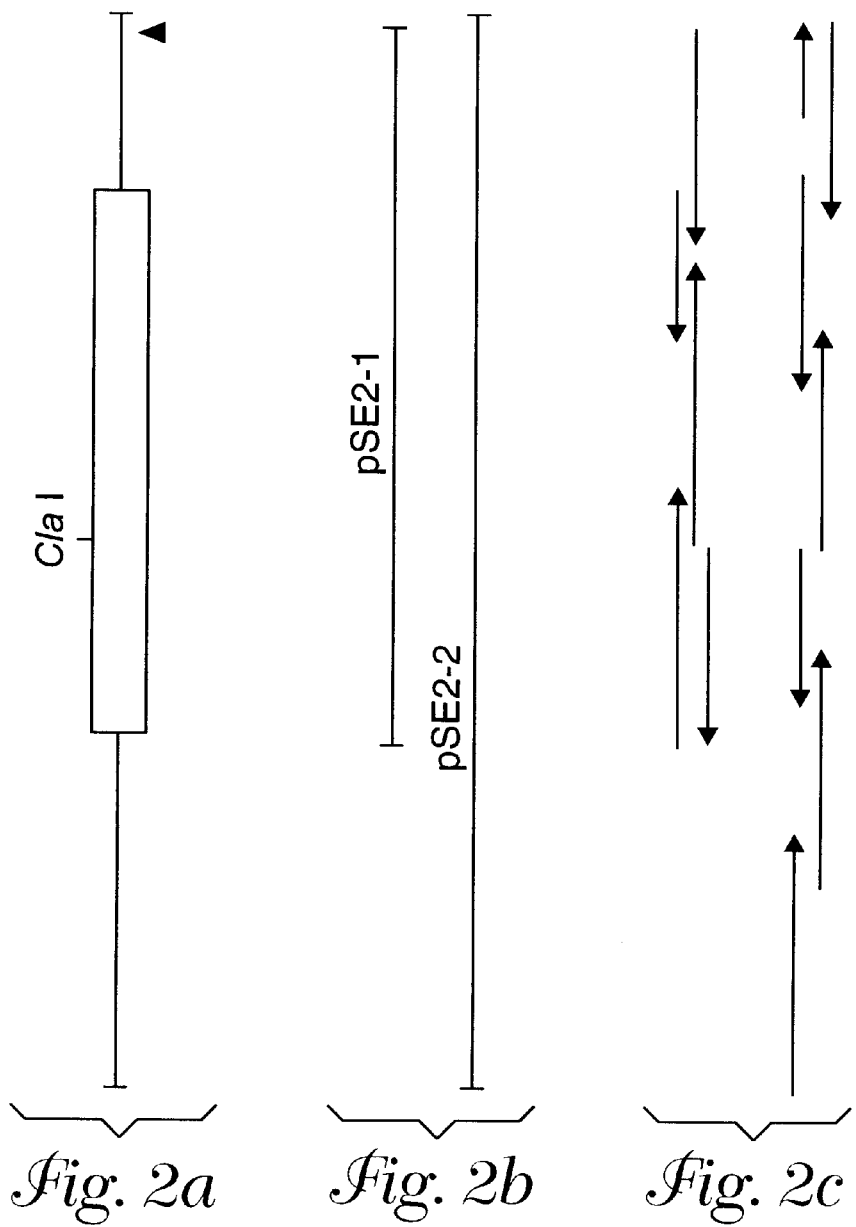
*Fig. 2a*  *Fig. 2b*  *Fig. 2c*

```
SEQ ID NO:1    1  GAATAATCCA  TTCGTTTATT  TTATGATGGA  TTCCTCCCAC  AACGGGGCCC
              51  TTGTATATTT  TATACATTCC  AGTGTATACA  AAATTTCTGG  CGGACGCTTC
             101  TTTAGGTCTA  AAGATATATG  CGCCGGATGA  CCTATTAACG  AAGACCTCAT
             151  TATTACCCTC  TGCTCCTACG  TAGTAATGGA  AGGATTGTAC  GACATTCAGG
             201  TCTCGATCAT  TCCACTTTAT  CATTAAGTTA  CCATCAGTGT  TAACAGATAT
             251  ATTAAACATC  TCATTGCTTA  TATAGTTGGT  TGGTTCAGAT  TGTTCAACTA
             301  CATTTTCCTG  CGCCTTTTTT  CTAACTACAT  AAGCTCGTAC  ACTGAGCGGA
             351  GGAATATAGT  TAGCACGGAA  GACGAGCTCA  TTTTTCGCAT  TGCTTTTTCT
             401  CCCTGGGATT  TTCTGAACTT  CATCGGCACG  AGCTCGTGCC  GCATTAACCA
```
```
             451  TGCTACCATT  CATTTTCTTA  GTGGTCGGCG  TTCTTGCACA  ACAGACGTTT
SEQ ID NO:2        M   L   P    F   I   F   L    V   V   G    V   L   A    Q   Q   T   F    -7
             501  GCTGAGGAAC  CCGAGAAGAT  CGTCGGTGGC  CAAGATGCCG  CACCAGGCGA
                   A   E   E    P   E   K   *I  V   G   G    Q   D   A    A   P   G      10
             551  ATTTCCGCAT  CAAGGTTCCT  TGAGATTGCG  AGGCTCACAC  ATTTGTGGCT
                   E   F   P   H    Q   G   S    L   R   L    R   G   S   H    I   C   G   27
             601  GCTCCATCAT  CGGCCCGAAG  ACAATCTTGA  CTGCCGCTCA  TTGCGTGGAT
                   C   S   I    I   G   P   K    T   I   L    T   A   A    H   C   V   D   44
             651  GGTATCGCAG  AATATCCTTA  TAGTAACTTC  AAGGTTGTGA  CCGGCACCAT
                   G   I   A    E   Y   P    Y   S   N   F    K   V   V    T   G   T      60
             701  CGATAGATAT  ACGGGAGGAG  AGACCCACGA  TGTGAAGAGC  GTTCACGTGC
                   I   D   R   Y    T   G   G    E   T   H    D   V   K   S    V   H   V   77
             751  ATCCGTATTA  TTCCGACAGA  GTGGAAGATG  CTTGGGTGAA  TGATGTTGCA
                   H   P   Y    Y   S   D   R    V   E   D    A   W   V    N   D   V   A   94
             801  GTGATCACGC  TTAAATCGGC  GATTAAGTAC  AACCAGTATC  AAAAACCGAT
                   V   I   T    L   K   S    A   I   K   Y    N   Q   Y    Q   K   P      110
             851  TGCCCTGGCC  AAGACCCGAC  CCGCTGACGG  AACCCAATGT  CAATTGTCCG
                   I   A   L    K   T   R    P   A   D    G   T   Q   C    Q   L   S      127
             901  GATGGGGTCA  GATCAGCACG  AACGGACCGC  TTCCGCGCAT  TCTCCAAAAG
                   G   W   G    Q   I   S   T    N   G   P    L   P   R    I   L   Q   K   144
             951  ATGTTCCAGG  TCATATACAA  TCAGGAAAAA  TGCAAGCAAC  GTCATAATAT
                   M   F   Q    V   I   Y    N   Q   E   K    C   K   Q    R   H   N      160
            1001  GCCTTTAACT  GGCAGTCACG  TGTGCGCGTA  TAACCGCTAC  GGAATTGGCG
                   M   P   L   T    G   S   H    V   C   A    Y   N   R   Y    G   I   G   177
            1051  CTTGTTCCGG  TGACAGCGGT  GGTCCGCTCA  TCTGCGGTGG  CGTACAGTGC
                   A   C   S    G   D   S   G    G   P   L    I   C   G    G   V   Q   C   194
            1101  GGTATTACTT  CCTGGGTTCT  TCCTTGCGCA  AAGGGTGAGC  CTGATGCCTA
                   G   I   T    S   W   V    L   P   C   A    K   G   E    P   D   A      210
            1151  CACCAGTGTC  GCTTATCATT  ACGACTTTAT  TGAACAATAT  TTAGAATAAA
                   Y   T   S   V    A   Y   H    Y   D   F    I   E   Q   Y    L   E   -   226
            1201  TCTATTTGAT  GGTATTGTCA  ATGGAAACAA  TGGATGTCAA  CGCGTCGAAA
            1251  GAATACGATG  CGTTGGTTAC  GTTTTTGAAA  AAGAAGAATA  TACTTCTGTA
            1301  CTTACAATAT  AAATAAATAA  ATAAAACAGT  TTAGTTAAA   TCTAAAAAAA
            1351  AAAAAAAAAA  AA
```

*Fig. 3*

```
SEQ ID NO:
2  Soli E2     mlpfiflvv------gvlaqqtfaeepekIVGGQDAAPGEFPHQGSLRLRGSHICGCSIIGPKTILTAAH      41
3  O. Hornet   ---------------------------------IVGGTDAPRGKYPYQVSLRA-PKHFCGGSI-SKRYVLTAAH   39
4  Fruit Fly   mlkfvillsavacalggtipegllpqldgrIVGGTATTISSFPWQISLQRSGSHSCGGSIYTDRVIVTAAH     41
5  Mosquito    mnqflfvsf---calldsakvsaatlssgrIVGGFQIDIAEVPHQVSLQRSGRHFCGGSIISPRWVLTRAH     41
6  HLE         mtlgrrlaclflacvlpal-llggtalaseIVGGRRARPHAWPFMVSLQLRGGHFCGATLIAPNFVMSAAH     41
                                                              *

Soli E2     CVDGIAEYPYSNFKVTGTIDRYTGGETHDVKSVHVHPYYSD-RVEDAWVNDVAVITLKSAIKYNQYQKPI     111
   E. Hornet   CLVGKSKHQVT---VHAGSVLLNKEEAVYNAEELIVNKNYNSIRL---INDIGLIRVSKDISYTQLVQPV     103
   Fruit Fly   CLQSVSA---SSLQIRAGSSYWSSGGVTVKVSSFKNHEGYNP----NTMVNDIAVIRLSSLGFSSTIKSI   105
   Mosquito    CTTNTDPAAYT---IRAGSTDRTNGGIIVKVKSVIPHPQYNG----DTYNYDFSLLELDESIGFSRSIEAI   105
   HLE         CVANVNVRAVRVVLGAHNLSRREPTRQVFAVQRIFENG-YDPVNL---LNDIVILQLNGSATINANVQVA   107
                                                   *

Soli E2     ALAKTRPAD--GTQCQLSGWG-QISTNGPLPRILQKMFQVIYNQEKCKQRHNMPLTGSHVCAYNRY---GI   176
   E. Hornet   KLPVSNTIKA-GDPVVLTGWG-RIYVNGPIPNNLQQITLSIVNQQTGKFKH-WGLTDSQICTFTKL---GE   168
   Fruit Fly   SLASSNPAN--GAAASVSGWGTQSSGSSSIPSQLQYVNVNIVSQSKCASSAYGYGSEIRNTNICAAAS-GK   173
   Mosquito    ALPDASETVADGAMCTVSGWG-DTKNVFEMNTLLRAVNVPSYNQAECAAALVNVVPVTEQMICAGYAAGGK   175
   HLE         QLPAQGRRLGNGVQCLAMGWG-LLGRNRGIASVLQELNVTVTVTSL-GRRSNV------CTLVRGRQAG-   167

Soli E2     GACSGDSGGPLICGGVQCGITSWVL-PCAKGE-PDAYTSVAYHYDFIEQYLE------              226
   E. Hornet   GACDGDSGTPLVANGVQIGIVSYGH-PCAVGS-PNVFTRVYSFLDWIQKNQL------              218
   Fruit Fly   DACQGDSGGPLVSGGPLVSGDKLVGVVSWGY-GCAYSNYPGVYASVADLRSWVINNA-              223
   Mosquito    DSCQGDSGGPLVSGDKLVGVVSWGK-GCALPNLPGVYARVSTVRQWIREVSEV----              227
   HLE         -VCFGDSGSPLVQNGLIHGIASFVRGGCASGLYPDAFAPVAQFVNWIDSIIQRSEDNPCPHPRDPDPASRTH  238
```

Fig. 4

ANT PROTEASES AND METHODS OF INHIBITION

CONTINUING APPLICATION DATA

This application claims the benefit of U.S. Provisional Application Ser. No. 60/136,331, filed May 27, 1999, which is incorporated by reference herein.

STATEMENT OF GOVERNMENT RIGHTS

The present invention was developed with support by National Institutes of Health Grant No. HL26148. The government may have certain rights in the invention.

BACKGROUND

Of the species of ants present in the United States, *Solenopsis richteri* and *Solenopsis invicta*, commonly referred to as the imported black fire ant and imported red fire ant, respectively, are not indigenous to North America. Both of these species are indigenous to the riverbanks of the Paraguay and Guapore regions of South America. *S. geminata* is a fire ant that is indigenous to North America.

The imported red fire ant (*Solenopsis invicta*), a major pest in the Southern United States, has had a large medical and economic impact because of its effects on man, livestock, and agriculture in general. For example, a study at the University of Texas, on a 70-acre tract of land, showed that as *S. invicta* moved across the effect was on the whole insect fauna. The number of other ant species declined by 70%, while a number of arthropod species, such as spiders, ticks, and other insects, dropped by 40%. It has been noted that fire ants are able to damage the roots of various crops, girdle the stems of young citrus trees, as well as feed on the fruits and flowers of several plants, particularly okra.

The most noticeable concern imposed by *S. invicta* is its physical and medical impact on man. Fire ants are a major nuisance to humans and other animals due to their powerful, painful sting, from which the name was acquired. In *S. invicta*, 95% of the venom consists primarily of alkyloids (2,6-disubstituted piperidines). Allergic reactions which can lead to death from anaphylactic shock occur in 1–2% of the population. A 1989 survey announced that 32 persons died from fire ant stings, most of which involved less than five stings. Due to the prevalence of *S. invicta*, man cannot help but encounter them in any outdoor activity, resulting in between 67,000–85,000 people per year seeking medical treatment for fire ant stings.

In 1957, when it became apparent that fire ants posed a serious problem, the federal government launched a massive campaign to eliminate this pest. In five years, the United States government spent 70 million dollars dispensing chlordane, dieldrin and heptachlor over large areas. While these three poisons did kill fire ants, they also had adverse effects to a variety of other organisms, including the native ant fauna. Also, due to their stability, these compounds were soon detected in the environment and were found to be responsible for the death of birds, fish and reptiles. In view of this, the use of these chemicals immediately ceased. A few years later in the mid-sixties, the compound mirex was developed. It proved effective against *S. invicta*, but unfortunately, it was also found to be capable of killing all species of ants. Nonetheless, since mirex appeared to have minimal environmental effects and eradication seemed economically feasible, this poison was broadly employed to control fire ant infestation. However, after several years of use, low levels of residues were detected in some non-target organisms. Perhaps more significantly, remnants of this poison were found in adipose tissue from humans and studies suggested that mirex might be a carcinogen. Therefore, in 1978, the Environmental Protection Agency revoked the use of mirex, thus, ending the widespread distribution of this poison. Since that decision there has never been a more intensive effort to control an unwanted pest in the United States.

When the above poisons were used to fight the fire ant infestation, the indigenous species of ants, which happen to be the best defense against the fire ant, were also killed. By eliminating the fire ant's competition, in combination with their aggressiveness and high rate of reproduction, man played to the strength of *S. invicta* by clearing the way for it to invade the North American habitat.

Currently, the most common methods of treating fire ant infestation include the use of toxicants (amidohydrozones), juvenile hormone analogs, or avermectin $B_1a$. However, in order to eliminate the colony completely it is necessary to kill the queen, and with the emergence of polygyne (multiple queen) colonies this has become more difficult. Juvenile hormone analogs interfere with the development of the brood, but the entire colony must be reached or it will quickly rebound. It has been observed that sometimes the colony will relocate in response to physical disturbance or stress if members of the colony suddenly die. Therefore a subtler and less invasive means of control would be useful.

In the course of maturation, the fire ant undergoes eight stages of development: egg—1st, 2nd, 3rd and 4th instar larvae—prepupae—pupae—adult. The 4th instar larvae plays an important role in the survival of the colony in that it is totally responsible for the digestion of solid foods and the source of nutrients for the queen and adult workers. It has been proposed that proteinase inhibitors might be a method for controlling undesirable insects; however, the use of non-specific inhibitors that inhibit a large number of ant proteolytic enzymes may cause a colony to relocate. Travis et al. (*Acta Biochemica Polonica*, 43, 411–417 (1996)) disclose in a review the existence of three proteolytic enzymes isolated from the 4th instar larvae of *S. invicta*. However, the purification steps are not disclosed in sufficient detail to allow purification of the proteolytic enzymes.

SUMMARY OF THE INVENTION

The present invention represents a potential advance in the control and/or eradication of fire ants by describing the purification and characterization of fire ant proteinases. The present invention provides isolated polypeptides, preferably isolated from an ant, particularly a *S. invicta* 4th instar larvae, having amidolytic activity for cleavage of a peptide bond present in a target polypeptide. In particularly preferred embodiments, four proteinases have been successfully isolated from the 4th instar larvae of *S. invicta* and characterized. Based on substrate specificity, they appear to represent two chymotrypsin-like and two elastase-like proteinases. These are referred to as Soli C1, Soli C2, Soli E1, and Soli E2, respectively, and have molecular weights of 25, 28, 23, and 24 kDa, respectively, based on SDS-PAGE. All enzymes are inhibited by diisopropyl fluorophosphate, a general serine class inhibitor. Each enzyme has been characterized as to pH optimum, pH stability, isoelectrofocusing, and susceptibility to inhibition by a broad range of natural and synthetic proteinase inhibitors. Such compounds may prove useful for the development of insecticides to control fire ant infestation.

In preferred embodiments, the polypeptide can have an elastase-like amidolytic activity, and can cleave a target polypeptide of MeOSuc-Ala-Ala-Pro-Val-pNA (SEQ ID NO:8), where the polypeptide and target polypeptide are in about 0.05 M Tris-HCl, about 100 mM NaCl at about pH 7.4 and about 25° C. for about 10 minutes. In other preferred embodiments, the polypeptide can have a chymotrypsin-like amidolytic activity, and can cleave a target polypeptide of Suc-Ala-Ala-Pro-Phe-pNA (SEQ ID NO:7), where the polypeptide and target polypeptide are in about 0.05 M Tris-HCl, about 100 mM NaCl at about pH 7.4 and about 25° C. for about 10 minutes. The polypeptide can include an amino terminal amino acid sequence of SEQ ID NO:25, SEQ ID NO:26, SEQ ID NO:27, or SEQ ID NO:28.

The invention is also directed at an isolated polypeptide, an active analog or an active fragment thereof, where the polypeptide includes an amino acid sequence that has a percentage amino acid identity of greater than 39% with SEQ ID NO:2, or alternatively including the amino acid sequence of SEQ ID NO:2, an active analog or an active fragment thereof.

Another aspect of the invention is an isolated nucleic acid fragment encoding a polypeptide, where the nucleic acid fragment has a nucleotide sequence including nucleotides 519 to 1198 of SEQ ID NO:1, and a complement thereto. Alternatively, the nucleic acid fragment of the invention is a complement of the nucleic acid fragment that hybridizes to nucleotides 519 to 1198 of SEQ ID NO:1 under hybridization conditions of: a solution of 5 x Denhardt's solution, 0.12 M phosphate buffer, pH 6.8 and 3 x SSC, at 47° C. for about 12 hours, followed by two washes in a solution of 1 x SSC and 0.1% SDS for 20 minutes at 42° C., and two washes in a solution containing 1 x SSC for 20 minutes at 42° C., and a complement to the nucleic acid fragment.

The invention further provides an isolated polypeptide having chymotrypsin-like amidolytic activity for cleavage of a peptide bond present in a target polypeptide, where the polypeptide includes an amino terminal amino acid sequence selected from the group consisting of SEQ ID NO:25 and SEQ ID NO:26.

Alternatively, an isolated polypeptide having chymotrypsin-like amidolytic activity for cleavage of a peptide bond present in a target polypeptide is isolated from a *Solenopsis invicta* 4th instar larvae. An isolated polypeptide having chymotrypsin-like amidolytic activity isolated from a *Solenopsis invicta* 4th instar larvae can have a molecular weight of about 25 kDa or about 28 kDa as determined by sodium dodecyl sulfate polyacrylamide gel electrophoresis. An isolated polypeptide having chymotrypsin-like amidolytic activity isolated from a *Solenopsis invicta* 4th instar larvae can include an amino terminal amino acid sequence selected from the group consisting of SEQ ID NO:25 and SEQ ID NO:26.

The invention further provides an isolated polypeptide having elastase-like amidolytic activity for cleavage of a peptide bond present in a target polypeptide, where the polypeptide includes an amino terminal amino acid sequence selected from the group consisting of SEQ ID NO:27 and SEQ ID NO:28.

Alternatively, an isolated polypeptide having elastase-like amidolytic activity for cleavage of a peptide bond present in a target polypeptide is isolated from a *Solenopsis invicta* 4th instar larvae. An isolated polypeptide having elastase-like amidolytic activity isolated from a *Solenopsis invicta* 4th instar larvae can have a molecular weight of about 23 kDa or about 24 kDa as determined by sodium dodecyl sulfate polyacrylamide gel electrophoresis. An isolated polypeptide having elastase-like amidolytic activity isolated from a *Solenopsis invicta* 4th instar larvae can include an amino terminal amino acid sequence selected from the group consisting of SEQ ID NO:27 and SEQ ID NO:28.

An aspect of the invention includes methods of identifying a molecule that inhibits an amidolytic activity of a *Solenopsis invicta* 4th instar larvae polypeptide. The methods include incubating a polypeptide of the present invention with the molecule under conditions that promote amidolytic activity and determining if the amidolytic activity of the polypeptide of the present invention is inhibited (i.e., the level and/or rate of activity is at least partially decreased) relative to the amidolytic activity in the absence of the molecule. The polypeptide can be an isolated polypeptide having amidolytic activity for cleavage of a peptide bond present in a target polypeptide, where the polypeptide is isolated from an ant. Alternatively, the polypeptide can be an isolated polypeptide, an active analog or an active fragment thereof, the polypeptide including an amino acid sequence having a percentage amino acid identity of greater than 39% with SEQ ID NO:2. In another embodiment the polypeptide can be a polypeptide including an amino terminal amino acid sequence selected from the group consisting of SEQ ID NO:25, SEQ ID NO:26, SEQ ID NO:27, and SEQ ID NO:28.

Another aspect of the invention is a method of reducing the amidolytic activity of at least one polypeptide used in the digestion of solid foods by a *Solenopsis invicta* 4th instar larvae including contacting the at least one polypeptide with an inhibitor of the at least one polypeptide, wherein the at least one polypeptide comprises an amino terminal amino acid sequence selected from the group consisting of SEQ ID NO:25, SEQ ID NO:26, SEQ ID NO:27, and SEQ ID NO:28. Preferably, the amidolytic activity of one polypeptide is inhibited.

The invention also includes a method of reducing the amount of solid food digested by a *Solenopsis invicta* 4th instar larvae including introducing an inhibitor to a *Solenopsis invicta* colony, where the inhibitor reduces the amidolytic activity of at least one polypeptide comprising an amino terminal amino acid sequence selected from at least one of the group consisting of SEQ ID NO:25, SEQ ID NO:26, SEQ ID NO:27, and SEQ ID NO:28.

Definitions

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether synthetic or naturally occuring. This term also includes post-expression modifications of the polypeptide, for example, glycosylations, acetylations, phosphorylations, and the like.

"Protease," "proteinase," "peptidase," and "proteolytic enzyme" all refer to a polypeptide that catalyzes the hydrolysis of peptide bonds in a polypeptide. A "peptide bond" or "amide bond" is a covalent bond between the alpha-amino group of one amino acid and the alpha-carboxyl group of another amino acid. "Peptidase inhibitor," "proteinase inhibitor," "protease inhibitor," and "inhibitor" all refer to molecules that inhibit a protease that catalyzes the hydrolysis of peptide bonds in a polypeptide.

As used herein, the term "isolated" means that a nucleic acid fragment or polypeptide is either removed from its natural environment or synthetically derived. Preferably, the nucleic acid fragment or polypeptide is purified, i.e., essentially free from any other nucleic acid fragments or polypeptides and associated cellular products or other impurities. "Amidolytic activity" and "protease activity" refer to the ability of a polypeptide to catalyze the hydrolysis of at least one peptide bond in a polypeptide. The term "cleavage" can also be used to refer to the hydrolysis of a peptide bond in a polypeptide. A polypeptide having "chymotrypsin-like" amidolytic activity is a polypeptide having amidolytic activity similar to chymotrypsin in that it cleaves a peptide bond in substrates having a P1 residue of leucine or phenylalanine. A polypeptide having "elastase-like" amidolytic activity is a polypeptide having amidolytic activity similar to pancreatic elastase in that it cleaves a peptide bond in substrates having a P1 residue of alanine or valine. P1 refers to the amino acid residue immediately upstream of the cleaved peptide bond.

A "target polypeptide" is a polypeptide that is the potential substrate for the amidolytic activity of a protease.

An "active analog" or "active fragment" of a polypeptide of the invention is one that has amidolytic activity by hydrolysis of a peptide bond present in the target polypeptide as described herein. Active analogs and active fragments are described in greater detail herein.

"Nucleic acid fragment" as used herein refers to a linear polymeric form of nucleotides of any length, either ribonucleotides or deoxynucleotides, and includes both double- and single-stranded DNA and RNA. A nucleic acid fragment may include both coding and non-coding regions that can be obtained directly from a natural source (e.g., an ant), or can be prepared with the aid of recombinant or synthetic techniques. A nucleic acid molecule may be equivalent to this nucleic acid fragment or a nucleic acid molecule can include this fragment in addition to one or more other nucleotides or polynucleotides. For example, a nucleic acid molecule of the invention can be a vector, such as an expression or cloning vector.

"Percentage amino acid identity" and "percentage nucleic acid identity" refer to a comparison of the amino acids of two polypeptides or a comparison of the nucleotides of two nucleic acid sequences, respectively, as described herein.

"Ant" as used herein refers to social insects of the family Formicidae, typically having wings only in the males and fertile females, and living in colonies that have a complex social order. "Ant" includes all developmental stages; egg, 1st instar larvae, 2nd instar larvae, 3rd instar larvae, 4th instar larvae, prepupae, pupae, and adult.

Unless otherwise specified, the indefinite article "a" or "an" means one or more.

BRIEF DESCRIPTION OF THE DRAWINGS

FIG. 2. Restriction map of Soli E2 cDNA: (a) Restriction map and organization of Soli E2 cDNA, the coding region is boxed and the arrow denotes the polyadenylation signal; (b) Isolated clones coding for Soli E2; (c) sequencing strategy.

FIG. 3. Nucleotide and deduced amino acid sequence of Soli E2: The primary nucleotide sequence (numbered on the left) and deduced amino acid sequence by the single letter code (numbered on the right) are shown (SEQ ID NO:1 and SEQ ID NO:2, respectively); an open reading frame extends from the translational start site (ATG) to the termination site (TAA); this is flanked by 5' and 3'-untranslated regions that ends with a polyadenylation signal (underlined) and the poly(A) tail; the shaded circles indicate the catalytic triad and the asterisk shows the proteolytic processing site; the degenerate oligonucleotide was designed against the region in the shaded box.

FIG. 4. Alignment of the deduced amino acid sequence of Soli E2 with other known proteinases: Alignment using TFASTA and LALIGN were based on the sequence of Soli E2 (SEQ ID NO:2), with appropriate gaps; identical residues to Soli E2 are displayed in shaded boxes; asterisks indicate the active site catalytic triads. Disulfide bonds of HLE are shown as well as the residues that line the active site pocket. O. Hornet, oriental hornet chymotrypsin II (SEQ ID NO:3); Fruit Fly, fruit fly β trypsin (SEQ ID NO:4); Mosquito, yellow fever mosquito trypsin 31A (SEQ ID NO:5); and HLE, human leukocyte elastase (SEQ ID NO:6).

DETAILED DESCRIPTION OF THE INVENTION

Figure 1A:
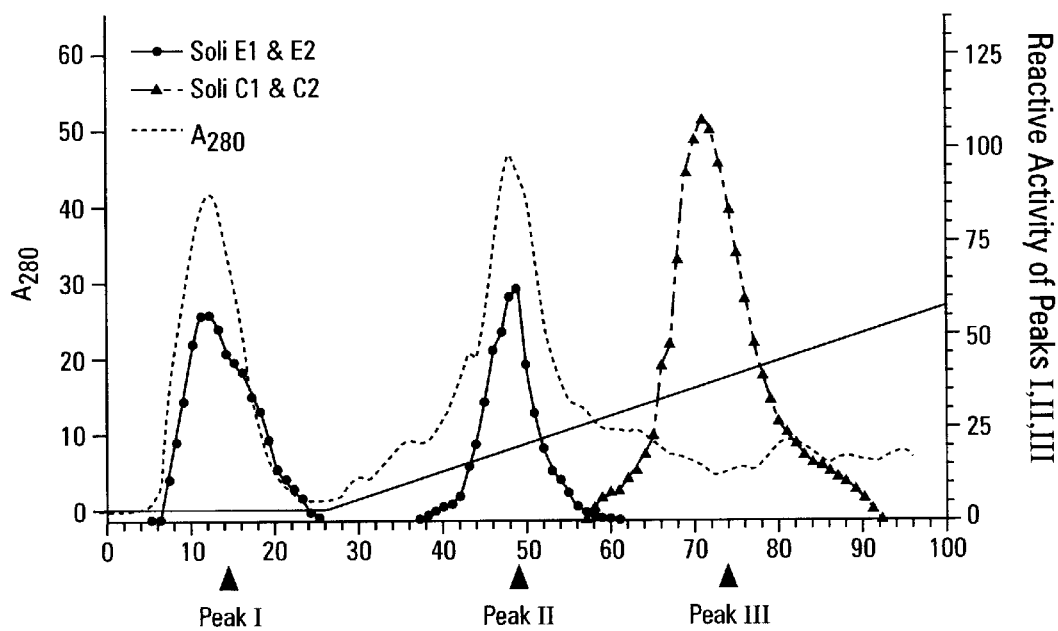
FIG. 1. Chromatography of *S. invicta* larvae acetone powder extracts. (a) chromatograph of crude extracts on Q Sepharose; (b) chromatograph of Peak III on Mono Q to separate Soli C1 and Soli C2.

The present invention provides isolated polypeptides, preferably proteases, and more preferably serine proteases. Examples of serine proteases include, for instance, chymotrypsin-like proteases and elastase-like proteases. The polypeptides can be isolated from 3rd or 4th instar larvae of ants, preferably the 4th instar stage. Preferably, the ant is a fire ant, more preferably *S. geminata, S. richteri* or *S. invicta*, most preferably *S. invicta*. Alternatively, the polypeptides can include an amino terminal amino acid sequence that includes SEQ ID NO:25, SEQ ID NO:26, SEQ ID NO:27, or SEQ ID NO:28, as listed in Table V herein. The isolated polypeptides are important in the digestion of polypeptides, preferably polypeptides present in solid foods, by the 4th instar larvae. The present invention provides methods of identifying inhibitors of the isolated proteases, methods of reducing the activity of the isolated proteases, and methods of reducing the amount of solid food digested by a 4th instar larvae. Preferably, the inhibitors used in the methods at least partially decrease (i.e., reduce), and more preferably substantially completely reduce (i.e., the activity is undetectable using currently available detection methods), the activity of a polypeptide of the present invention. The present invention also provides methods of inhibiting (at least partially and preferably completely) the viability of ants.

Typically, the amidolytic activity of a polypeptide of the invention is inhibited by molecules that typically inhibit serine proteases, including for instance diisopropylfluorophosphate (DFP). Typically, the amidolytic activity of a polypeptide of the invention is not inhibited by molecules that typically do not inhibit serine proteases, including for instance trans-epoxysuccinyl-L-leucylamido-(4-guanidino) butane (E-64), ethylenediaminetetraacetate·$2H_2O$ (EDTA), and pepstatin. Synthetic peptide inhibitors that can inhibit the amidolytic activity of the polypeptides of the present invention include, for example, IsoVal-Phe-CK, Z-Pro-Val-$^P$(OPh)$_2$, Z-Val-Val-$^P$(OPh)$_2$, Boc-Ala-Pro-Val-$^P$(OPh)$_2$, Boc-Val-Pro-Val-$^P$(OPh)$_2$, and DCIC. Naturally occurring protease inhibitors that can inhibit the amidolytic activity of the polypeptides of the present invention include, for example, Elgin C, soy bean trypsin inhibitor I-S, α1-PI, potato inhibitor I, and potato inhibitor II.

Target polypeptides of the chymotrypsin-like polypeptides of the invention include Suc-Phe-Leu-Phe-pNA, Suc-Phe-Pro-Phe-pNA, Suc-Phe-Val-Phe-pNA, Suc-Ala-Ala-Pro-Leu-pNA (SEQ ID NO:10), Suc-Ala-Ala-Pro-Met-pNA (SEQ ID NO:11), Suc-Phe-Ala-Ala-Phe-pNA (SEQ ID NO:12), Suc-Ala-Ala-Pro-Phe-pNA (SEQ ID NO:7), Suc- Ala-Leu-Pro-Phe-pNA (SEQ ID NO:13), Suc-Ala-Phe-Pro-Phe-pNA (SEQ ID NO:14), Suc-Glu-Val-Pro-Phe-pNA (SEQ ID NO:15), Suc-Leu-Val-Pro-Phe-pNA (SEQ ID NO:16), Suc-Met-Val-Pro-Phe-pNA (SEQ ID NO:17), Suc-Phe-Val-Pro-Phe-pNA (SEQ ID NO:18), and HCl-Ile-His-t-Pro-Phe-pNA (SEQ ID NO:19). Preferably, the target polypeptide is Suc-Ala-Ala-Pro-Phe-pNA (SEQ ID NO:7).

Two chymotrypsin-like polypeptides have been isolated, and are referred to herein as Soli C1 and Soli C2. These polypeptides have molecular weights of about 25 kDa and about 28 kDa, respectively, as determined by SDS-PAGE. Soli C1 and Soli C2 have the amino terminal amino acid sequence of SEQ ID NO:25 and SEQ ID NO:26, respectively, as listed in Table V herein. Synthetic inhibitors with a P1 residue of phenylalanine typically inhibit Soli C1 and Soli C2 more efficiently than other synthetic inhibitors. Naturally occurring protease inhibitors that are members of the ovomucoid (OM) family, including for instance Canadian Goose OM, Canadian Goose OM Domain III, Domestic Goose OM, and Domestic Goose OM Domain III, typically do not inhibit the amidolytic activity of the chymotrypsin-like polypeptides of the present invention.

Target polypeptides of the elastase-like polypeptides of the invention include Suc-Ala-Pro-Ala-pNA, Suc-Ala-Ala-Val-Ala-pNA (SEQ ID NO:9), and MeOSuc-Ala-Ala-Pro-Val-pNA (SEQ ID NO:8). Preferably, the target polypeptide is MeOSuc-Ala-Ala-Pro-Val-pNA (SEQ ID NO:8).

Two elastase-like polypeptides have been isolated, and are referred to herein as Soli E1 and Soli E2. These polypeptides have molecular weights of about 23 kDa and about 24 kDa, respectively, as determined by SDS-PAGE. Soli E1 and Soli E2 have the amino terminal amino acid sequence of SEQ ID NO:27 and SEQ ID NO:28, respectively, as listed in Table V herein. The nucleotide sequence of the coding region encoding Soli E2 and the amino acid sequence of Soli E2 have been determined and are described herein. Synthetic inhibitors with a P1 residue of valine typically inhibit Soli E1 and Soli E2 more efficiently than other synthetic inhibitors. Naturally occurring protease inhibitors that are members of the ovomucoid family, including for instance Canadian Goose OM, Canadian Goose OM Domain III, Domestic Goose OM, and Domestic Goose OM Domain III, typically do inhibit the amidolytic activity of the elastase-like polypeptides of the present invention.

The polypeptides of the present invention, preferably elastase-like proteases and chymotrypsin-like proteases, can be isolated from fire ant 3rd or 4th instar larvae, preferably 4th instar. Preferably, the fire ant is *S. invicta*. The larvae are distinguished from other developmental stage instars by size and degree of development. The larvae can be collected from natural populations of ants or from colonies maintained in a laboratory.

As described herein, an example of an elastase-like polypeptide is Soli E2 isolated from a *S. invicta* 4th instar larvae (SEQ ID NO:2). The amino acid sequence of Soli E2 contains a catalytic triad typical of serine proteases, i.e., a histidine residue, aspartic acid residue, and a serine residue (at residues 41, 92, and 183, respectively, in the mature polypeptide, see FIG. 3). Soli E2 is a unique polypeptide, and the isolation and characterization of this novel polypeptide will facilitate the development of molecules that function to inhibit the amidolytic activity of this and/or other polypeptides isolated from ants, preferably fire ant 4th instar larvae, most preferably *S. invicta* 4th instar larvae.

The present invention therefore further includes polypeptides, preferably elastase-like polypeptides, having identity with the amino acid sequence of SEQ ID NO:2. The identity is referred to as percentage amino acid identity and is determined by aligning the residues of two amino acid sequences (i.e., a candidate amino acid sequence and the amino acid sequence of SEQ ID NO:2) to optimize the number of identical amino acids along the lengths of their sequences; gaps in either or both sequences are permitted in making the alignment in order to maximize the number of shared amino acids, although the amino acids in each sequence must nonetheless remain in their proper order. A candidate amino acid sequence is the amino acid sequence being compared to an amino acid sequence present in SEQ ID NO:2. A candidate amino acid sequence can be isolated from an ant, or can be produced using recombinant techniques, or chemically or enzymatically synthesized. Preferably, the two amino acid sequences (i.e., the candidate amino acid sequence and the amino acid sequence of SEQ ID NO:2) are aligned such that the residues that make up the catalytic triad, i.e., the histidine, aspartic acid, and the serine, (at residues 41, 92, and 183, respectively, in the mature polypeptide, see FIG. 3) are in register, then further aligned to optimize the number of identical amino acids along the lengths of their sequences. Preferably, two amino acid sequences are compared using the Blastp program, version 2.0.11, of the BLAST 2 search algorithm, as described by Tatiana, et al. (*FEMS Microbiol Lett* 1999, 174:247–250), and available at www.ncbi.nlm.nih.gov/gorf/b12.html. Preferably, the default values for all BLAST 2 search parameters are used, including matrix=BLOSUM62; open gap penalty=11, extension gap penalty=1, gap x_dropoff= 50, expect=10, wordsize=3, and filter on. In the comparison of two amino acid sequences using the BLAST search algorithm, percentage amino acid identity is referred to as "identities." Preferably, the amino acid sequence of an isolated polypeptide has a percentage amino acid identity with SEQ ID NO:2 of greater than about 39%, more preferably at least about 45%, most preferably at least about 50%.

The invention also can include an active analog or active fragment of a polypeptide such as that having the amino acid sequence of SEQ ID NO:2, one having a percentage amino acid identity of greater than 39% with SEQ ID NO:2, or one comprising an amino terminal amino acid sequence selected from the group consisting of SEQ ID NO:25, SEQ ID NO:26, SEQ ID NO:27 or SEQ ID NO:28. An active analog or active fragment preferably is characterized by substantially the same amidolytic activity properties with respect to a target polypeptide as is the polypeptide shown in SEQ ID NO:2; however, variations in the level or rate of amidolytic activity, for example, are allowed.

An active analog of the invention includes a polypeptide having one or more amino acid substitutions that do not eliminate amidolytic activity for a target polypeptide. For example, an active analog of the invention is characterized by the ability to cleave Suc-Ala-Pro-Ala-pNA, Suc-Ala-Ala-Val-Ala-pNA (SEQ ID NO:9), or MeOSuc-Ala-Ala-Pro-Val-pNA (SEQ ID NO:8), preferably MeOSuc-Ala-Ala-Pro-Val-pNA (SEQ ID NO:8).

Substitutes for an amino acid in the polypeptides of the invention may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Analogs, as used herein, also include modifications. Modifications of elastase-like polypeptides include an elastase-like polypeptide that is chemically or enzymatically derivatized at one or more constituent amino acid, including side chain modifications, backbone modifications, and N- and C- terminal modifications including acetylation, hydroxylation, methylation, amidation, and the attachment of carbohydrate or lipid moieties, cofactors, and the like. Modified elastase-like polypeptides of the invention will retain amidolytic activity with regards to a target polypeptide. For example, a modified elastase-like polypeptide of the invention will hydrolyze a peptide bond present in Suc-Ala-Pro-Ala-pNA, Suc-Ala-Ala-Val-Ala-pNA (SEQ ID NO:9), or MeOSuc-Ala-Ala-Pro-Val-pNA (SEQ ID NO:8), preferably MeOSuc-Ala-Ala-Pro-Val-pNA (SEQ ID NO:8).

Fragments of a polypeptide, such as that having the amino acid sequence of SEQ ID NO:2, one having a percentage amino acid identity of greater than 39% with SEQ ID NO:2, or one comprising an amino terminal amino acid sequence selected from the group consisting of SEQ ID NO:25, SEQ ID NO:26, SEQ ID NO:27 or SEQ ID NO:28, include a portion of the polypeptide containing deletions or additions of one or more contiguous or noncontiguous amino acids such that the resulting polypeptide still retains amidolytic activity with respect to a target polypeptide.

Isolation of a polypeptide from an ant larvae typically includes extracting larvae with a solution buffered at a pH of about 7.4 followed by purification methods that are well known in the art. The following are non-limiting examples of suitable protein purification procedures: fractionation on ion-exchange, hydroxyapatite, Phenyl-Sepharose HP, Q sepharose, Mono P, Mono Q, and Mono S columns; acetone precipitation and/or ethanol precipitation; reverse phase HPLC; chromatography on silica or on an ion-exchange resin such as DEAE; chromatofocusing; SDS-PAGE; ammonium sulfate precipitation; and gel filtration using, for example, Sephadex G-75. Preferably, isolation of a polypeptide from an ant larvae is accomplished using a combination of acetone precipitation and Q sepharose chromatography followed by either Mono S column chromatography or Mono Q column chromatography steps as described herein. Other optional steps can be used to further isolate a polypeptide as described herein. Alternatively, a polypeptide of the invention can be chemically synthesized using methods that are well known in the art including, for instance, solid phase synthesis.

Antibodies can be developed that bind to the polypeptides of the present invention and can be used to isolate the polypeptides by immunoaffinity fractionation. Such antibodies can also be used to determine if other types of ants (i.e., other genus and species) produce the polypeptides of the present invention. Without intending to be limiting, for instance proteins from extracts of other types of ants can be resolved by electrophoresis, transferred to a membrane and then exposed to antibodies.

If polyclonal antibodies are desired, a selected animal (e.g., mouse, rabbit, goat, horse or bird) is immunized with a polypeptide of the present invention. Serum from the immunized animal is collected and treated according to procedures well known in the art. If serum containing polyclonal antibodies to a polypeptide of the present invention contains antibodies to other antigens, the polyclonal antibodies can be purified by immuno-affinity chromatography. Techniques for producing and processing polyclonal antisera are known in the art, see for example, Mayer and Walker eds. *Immunochemical Methods in Cell and Molecular Biology* (Academic Press, London) (1987).

Monoclonal antibodies directed against a polypeptide of the present invention can be produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., Schreier et al. *Hybridoma Techniques,* (1980); Hammerling et al. *Monoclonal Antibodies and T-cell Hybridomas,* (1981); Kennett et al. *Monoclonal Antibodies* (1980); see also, U.S. Pat. Nos. 4,341,761 (Ganfield et al.); 4,399,121 (Albarella et al.); 4,427,783 (Newman et al.); 4,444,887 (Hoffmann); 4,466,917 (Nussenzweig et al.); 4,472,500 (Milstein et al.); and 4,491,632 (Wands et al.).

Whether a polypeptide of the present invention has amidolytic activity can be determined using methods known to the art. For instance, to determine whether a polypeptide has amidolytic activity, the polypeptide can be incubated with another polypeptide (i.e., a target polypeptide) known to be cleaved by either chymotrypsin-like proteases or by elastase-like proteases including, for instance, azo-casein or gelatin. Alternatively, the polypeptide can be incubated with different synthetic para-nitroanilide substrates. Preferably, a polypeptide of the present invention cleaves at least an amount of a target polypeptide that is detectable using available detection methods, more preferably cleaves at least about 10% of a target polypeptide present, even more preferably cleaves at least about 50% of a target polypeptide present, and most preferably cleaves substantially all of the target polypeptide present under the conditions described herein.

Typically, the concentration of the target polypeptide in a test solution is at least about 10 nM, preferably at least about 100 nM, and no greater than about 5 mM, preferably no greater than about 0.5 mM. The concentration in a test solution of the polypeptide of the present invention is typically at least about 1 nM to no greater than about 100 nM, preferably at least about 10 nM. When a synthetic inhibitor is present in a test solution, the concentration of the synthetic inhibitor is typically at least about 10 nM, preferably at least about 100 nM, and no greater than about 5 mM, preferably no greater than about 0.5 mM. When a naturally occurring protease inhibitor is present in a test solution, the concentration of the naturally occurring protease inhibitor is typically at least about 0.002 nM, preferably at least about 0.2 nM, and no greater than about 50 nM, preferably no greater than about 5 nM.

As different polypeptides have activity that depends on the buffer used for incubation, varying assay conditions can be used including, for instance, different pH, different salt concentrations, different types of salts, and different buffers. Non-limiting examples of assay conditions include about 150 mM NaCl and about 50 mM Tris-HCl at about pH 8.0, about 150 mM NaCl and about 50 mM CHES (2-(N-cyclohexylamino)ethanesulfonic acid) at about pH 9.5, about 150 mM NaCl and about 50 mM CAPS (3-(cyclohexylamino)-1-propanesulfonic acid) at about pH 10.0, and about 0.05 M Tris-HCl and about 100 mM NaCl at about pH 7.4. Preferably, the assay conditions for a polypeptide is about 0.05 M Tris-HCl, about 100 mM NaCl at about pH 7.4. Optionally, 10% to 20% $Me_2SO$ can be added to the buffer. Assays are typically conducted at about 25° C.

Polypeptide inhibition assays by synthetic and natural protein inhibitors can also be conducted in varying buffer conditions. Preferably, the assay conditions for polypeptide inhibition assays is about 0.05 M Tris-HCl and about 100 mM NaCl at about pH 7.4. Preferably, the concentration of an inhibitor is about 0.02 nM to about 50 nM and a polypeptide concentration of about 1.0 nM. Typically, the polypeptide inhibitor and polypeptide are preincubated for about 10 minutes. After addition of the target polypeptide, the time of incubation is about 1 minute to about 60 minutes, preferably about 10 minutes. Optionally, 10% to 20% $Me_2SO$ can be added to the buffer.

The coding region that encodes a polypeptide of the invention can be isolated from an ant, preferably from a 4th instar S. invicta larvae. A "coding region" is a linear form of nucleotides that encodes a polypeptide, usually via mRNA, when placed under the control of appropriate regulatory sequences. The boundaries of a coding region are generally determined by a translation start codon at its 5' end and a translation stop codon at its 3' end. "Regulatory region" refers to a nucleic acid fragment that regulates expression of a coding region to which a regulatory region is operably linked. Nonlimiting examples of regulatory regions include promoters, transcription initiation sites, translation start sites, translation stop sites, and terminators. "Operably linked" refers to a juxtaposition wherein the components so described are in a relationship permitting them to function in their intended manner. A regulatory element is "operably linked" to a coding region when it is joined in such a way that expression of the coding region is achieved under conditions compatible with the regulatory region.

Accordingly, the present invention is directed to a nucleic acid fragment encoding a polypeptide of the invention or its complement, particularly an elastase-like polypeptide, active analog, or active fragment thereof. Nucleic acid fragments can be isolated from ants, preferably 4th instar S. invicta larvae. The nucleic acid fragment can have a nucleotide sequence as shown in SEQ ID NO:1. Alternatively, nucleic acid fragments of the invention include those whose complement hybridize to SEQ ID NO:1 under the hybridization conditions as described herein. During hybridization the entire nucleotide sequence of the complement can hybridize with SEQ ID NO:1. Preferably, about 20 nucleotides of the complement hybridize with SEQ ID NO:1, more preferably about 50 nucleotides, most preferably about 100 nucleotides. "Complement" and "complementary" refer to the ability of two single stranded nucleic acid fragments to base pair with each other, where an adenine on one nucleic acid fragment will base pair to a thymine on a second nucleic acid fragment and a cytosine on one nucleic acid fragment will base pair to a guanine on a second nucleic acid fragment. Two nucleic acid fragments are complementary to each other when a nucleotide sequence in one nucleic acid fragment can base pair with a nucleotide sequence in a second nucleic acid fragment. For instance, 5'-ATGC and 5'-GCAT are complementary. The term complement and complementary also encompasses two nucleic acid fragments where one nucleic acid fragment contains a nucleotide that will not base pair to a nucleotide present on a second nucleic acid fragment. For instance the third nucleotide of each of the two nucleic acid fragments 5'-ATTGC and 5'-GCTAT will not base pair, but these two nucleic acid fragments are complementary as defined herein. Typically two nucleic acid fragments are complementary if they hybridize under the standard conditions referred to herein.

Alternatively, the nucleic acid fragment can have a nucleotide sequence encoding a polypeptide having the amino acid sequence shown in SEQ ID NO:2. An example of the class of nucleotide sequences encoding such a polypeptide is SEQ ID NO:1. This class of nucleotide sequences is large but finite, and the nucleotide sequence of each member of the class can be readily determined by one skilled in the art by reference to the standard genetic code.

The identification of coding regions encoding a polypeptide of the invention can be accomplished by screening nucleic acids isolated from ants, preferably 4th instar S. invicta larvae, for the presence of nucleotide sequences that are similar to the coding region of Soli E2 (i.e., nucleotides 519–1198 of SEQ ID NO:1). The nucleotides isolated from ants include, for example, genomic and cDNA libraries. Screening methods include, for instance, hybridization of a detectably labeled probe with a nucleic acid fragment. A probe can be a nucleic acid fragment that is complementary to SEQ ID NO:1. A probe is typically no greater than about 676 bases and no less than about 10 bases. Typically a probe does not hybridize under conditions described herein with nucleotides that are not part of a coding region of the present invention.

Another type of probe that can be used is a degenerate oligonucleotide probe (see, e.g.,, Sambrook et al., Molecular Cloning, A Laboratory Manual, 2nd edition, Cold Spring Harbor Laboratory Press, pp. 11.1–11.61 (1989)). Degenerate oligonucleotide probes can be obtained using the amino terminal amino acid sequence present in SEQ ID NO:25, SEQ ID NO:26, SEQ ID NO:27, or SEQ ID NO:28. For instance, the degenerate oligonucleotide 5'-CCYTGATGIGGRAAYTCNCC (SEQ ID NO:30) was derived from residues 10 to 16 of SEQ ID NO:28. A degenerate oligonucleotide probe is typically at least about 15 nucleotides to about 30 nucleotides. Preferably, a degenerate oligonucleotide probe is about 20 nucleotides. Degenerate oligonucleotide probes can be labeled using methods well known to the art. Hybridization conditions can vary depending on the composition of the nucleotides present in the degenerate oligonucleotide probe. Preferably, hybridization conditions are in 5 x Denhardt's solution, 0.12 M phosphate buffer, pH 6.8 and 3 x SSC, at 47° C. for about 12 hours, followed by two washes in a solution of 1 x SSC and 0.1% SDS for 20 minutes at 42° C., and two washes in a solution containing 1 x SSC for 20 minutes at 42° C.

A nucleic acid fragment identified by a probe (including by degenerate oligonucleotide probe) is further analyzed to determine if it encodes a polypeptide with amidolytic activity of a target polypeptide. Suitable target polypeptides are described herein. Another method for screening ants for the presence of nucleotide sequences that are similar to the coding regions of the present invention is the polymerase chain reaction (PCR).

Ants containing nucleic acid fragments encoding a polypeptide of the invention can also be identified using antibody. Preferably the antibody is directed to SEQ ID NOs:2, 25, 26, 27, or 28, or a portion thereof.

The use of hybridization of a probe to a coding region present in an ant can be used as a method to identify a coding region having identity to a coding region present in SEQ ID NO:1 (i.e., nucleotides 519–1198 of SEQ ID NO:1), or a coding region encoding SEQ ID NOs:25, 26, 27, or 28. The coding region can then be isolated and ligated into a vector as described below. The identity is referred to as percentage nucleic acid identity and is determined by aligning the residues of the two nucleic acid sequences (i.e., a nucleic acid sequence of a candidate coding region and the nucleic acid sequence of nucleotides 519–1198 of SEQ ID NO:1) to optimize the number of identical nucleotides along the lengths of their sequences; gaps in either or both sequences are permitted in making the alignment in order to optimize the number of identical nucleotides, although the nucleotides in each sequence must nonetheless remain in their proper order. A candidate coding region is the coding region being compared to a coding region present in SEQ ID NO:1 (i.e., nucleotides 519–1198 of SEQ ID NO:1), or a coding region encoding SEQ ID NOs:25, 26, 27, or 28. The nucleotide sequence of a candidate coding region can be isolated from an ant, or can be produced using recombinant techniques, or chemically or enzymatically synthesized. Preferably, two nucleotide sequences are compared using the Blastn program, version 2.0.11, of the BLAST 2 search algorithm, as described by Tatiana, et al. (*FEMS Microbiol Lett* 1999, 174:247–250), and available at www.ncbi.nlm.nih.gov/gorf/b12.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, percentage nucleic acid identity is referred to as "identities." Preferably, two nucleic acid sequences have, in increasing order of preference, at least about 90%, at least about 92%, at least about 94%, at least about 96%, and at least about 98% identity.

As mentioned above, a nucleic acid fragment of the invention can be inserted in a vector. Construction of vectors containing a nucleic acid fragment of the invention employs standard ligation techniques known in the art. See, e.g., Sambrook et al, Molecular Cloning: A Laboratory Manual, Cold Spring Harbor Laboratory Press (1989) or Ausubel, R. M., ed. Current Protocols in Molecular Biology (1994). A vector can provide for further cloning (amplification of the nucleic acid fragment), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK223-3, pKK233-2 and pTrc99A can be obtained from Pharmacia Biotech. pET-(X) vectors can be obtained from Promega (Madison, Wis.), Stratagene (La Jolla, Calif.), and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

An expression vector optionally includes regulatory regions operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

An expression vector can optionally include a Shine Dalgarno site (e.g., a ribosome binding site), and a start site (e.g., the codon ATG) to initiate translation of the transcribed message to produce the polypeptide. It can also include a termination sequence to end translation. A termination sequence is typically a codon for which there exists no corresponding aminoacetyl-tRNA, thus ending polypeptide synthesis. The nucleic acid fragment used to transform the host cell can optionally further include a transcription termination sequence. The rrnB terminators, which is a stretch of DNA that contains two terminators, T1 and T2, is an often used terminator that is incorporated into bacterial expression systems (J. Brosius et al., (1981) J. Mol. Biol. 148 107–127).

The nucleic acid fragment used to transform the host cell optionally includes one or more marker sequences, which typically encode a polypeptide that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, and tetracycline.

The present invention is also directed to a method of developing an inhibitor to a polypeptide of the present invention, preferably to a *S. invicta* 4th instar larvae polypeptide, or active analog or active fragment thereof, a polypeptide having a percentage amino acid identity of greater than 39% with SEQ ID NO:2, or to a polypeptide comprising an amino terminal amino acid sequence selected from the group consisting of SEQ ID NO:25, SEQ ID NO:26, SEQ ID NO:27, and SEQ ID NO:28. The method includes identifying a molecule that inhibits the amidolytic activity of the polypeptide. This can be accomplished, for instance, by incubating a polypeptide of the present invention with a candidate molecule under conditions that promote amidolytic activity of the polypeptide. If the amidolytic activity of the polypeptide is decreased relative to the amidolytic activity in the absence of the molecule, then the candidate molecule is an inhibitor of the polypeptide. The amidolytic activity can be measured by cleavage of a target peptide described herein. Preferably, an inhibitor is biodegradable.

Inhibitors developed in this way can be used to reduce the amidolytic activity of a polypeptide used in the digestion of solid foods by a *S. invicta* 4th instar larvae. Inhibitors developed in this way can also be used to reduce the amount of solid food digested by a *S. invicta* 4th instar larvae. Typically, an inhibitor can be suspended in water or a vegetable oil, for instance soybean oil or corn oil. The suspension is typically mixed with a compound containing protein, preferably, a compound that is porous such that it absorbs the suspension. Examples of porous compounds useful in this aspect of the invention are ground corn cobs (i.e., corn grit), dead flies, or rice. The resulting mixture of protein and suspension is referred to as bait, and can be spread (i.e., broadcast) around an ant mound. Alternatively or additionally, the bait can be placed in a bait station as described in, for instance, U.S. Pat. No. 5,746,021 (W. F. Green).

EXAMPLES

Objects and advantages of this invention are further illustrated by the following examples, but the particular materials and amounts thereof recited in these examples, as well as other conditions and details, should not be construed to unduly limit this invention.

Example 1

Isolation and Characterization of Four Serine Endoproteases

This Example demonstrates the purification and characterization of four distinctly different proteinases. Since secreted fluids from the anteroventural opening of the 4th instar larvae possessed the same amidolytic activity as the proteinases, it is likely that they are involved in the digestion of food for the colony. Egg, prepupae, pupae and adults when analyzed for these same putative digestive enzymes were found to be devoid of these proteinases, while the 1st, 2nd, and 3rd instar larvae possessed significantly lower levels of enzyme activity relative to the 4th instar larvae. Although it has been documented that adult ants do have a small amount of digestive enzymes in their midguts (A. A. Sorensen et al. *J. Insect Physiol.,* 29, 163–168 (1983)), the presence of these proteinases in adult ants is likely due to trophalaxis.

Characterization of these proteinases indicated a strong relationship towards other members of the pancreatic proteinase family, including Mr, substrate specificity, inhibition profile, and N-terminal sequence. The proteinases were classified as related to elastase and chymotrypsin. While each of the purified enzymes was identified, primarily, through the use of synthetic substrates (i.e., target polypeptides), all were also able to degrade both azo-casein and gelatin, thereby supporting the fact that they are, indeed, proteinases. All of the larvae-derived proteinases could be regulated by both synthetic and natural inhibitors, with the latter being from both plant and animal sources.

Materials and Methods

Suc-Ala-Ala-Pro-Phe-pNA (SEQ ID NO:7), MeOSuc-Ala-Ala-Pro-Val-pNA (SEQ ID NO:8), Nα-p-tosyl-L-lysine-chloromethyl ketone (TLCK), Nα-p-tosyl-L-phenylalanine chloromethyl ketone(TPCK), lima bean trypsin inhibitor (LBTI), soybean trypsin inhibitor Type I-S (SBTI), diethyl pyrocarbonate, and Trizma were from Sigma (St. Louis, Mo.). Diisopropyl fluorophosphate (DFP) was from Calbiochem (La Jolla, Calif.). Trasylol and α-1-Proteinase Inhibitor (α-1-PI) were gifts from Athens Research and Technology, Athens, Ga. Eglin C was obtained from Dr. Hans Schnebli of Ciba Geigy. Hen ovomucoid (OM), Canadian goose OM and domestic goose OM were graciously provided by Dr. Michael Laskowski (Purdue University, West LaFayette, Ind.). Potato inhibitors I and II were obtained from Dr. Clarence Ryan (Washington State University, Pullman, Wash.) All other pNA substrates and synthetic inhibitors were provided by Dr. James Powers (Georgia Institute of Technology, Atlanta).

The following abbreviations are used: Suc, succinyl; pNA, p-nitroanilide; MeOSuc, methoxy succinyl; TLCK, Nα-p-tosyl-L-lysine chloromethyl ketone; TPCK, Nα-p-tosyl-L-phenylalanine chloromethyl ketone; LBTI, lima bean trypsin inhibitor; SBTI; soy bean trypsin inhibitor; DFP, diisopropyl fluorophosphate; OM, ovomucoid; CAPS, 3-[cyclohexylamino]-1-propanesulfonic acid; CHES, 2-(N-cyclohexylamino)-ethanesulfonic acid; CHAPS, 3-[(3-cholamidopropyl)dimethylammonio]-1-propanesulfonate; Tricine, N-[2-hydroxy-1,1-bis(hydroxymethyl)ethyl] glycine; PAGE, polyacrylamide gel electrophoresis; E-64, trans-epoxysuccinyl-L-leucylamido-(4-guanidino)butane; Z, benzyloxycarbonyl; Boc, t-butoxycarboyl; IEF, isoelectricfocusing.

Cultivation of Larvae—The colonies of *S. invicta* were maintained according to R. S. Petralia et al. (*Ann. Entomol. Soc. Am.* 71, 643–648 (1978)), with the different stages of development being manually separated, using a dissecting microscope, based on that described by R. S. Petralia et al. (*Ann. Entomol. Soc. Am.* 72, 472–484 (1979)) and using an aspirator to draw larvae into a recepticle.

Enzyme purification—Fourth instar larvae were extracted in a 1:10 (weight/volume) ratio of 20 mM Tris-HCl pH 7.4, (Buffer A). Briefly, intact larvae were placed in buffer A, which results in the lysis of the cells of the larvae. The mixture was stirred at 4° C. for 24 hours and centrifuged at 10,000 x g, for 15 minutes at 4° C., with the lipid layer on top being removed physically by pipette and the supernatant retained. Chilled acetone was added at a 2:1 (volume/volume) ratio over a period of 15 minutes at 4° C. This produced a precipitate, which was collected by centrifugation (10,000 x g, 15 minutes, 4° C.). The precipitate was redissolved in 1/10 of its original volume in buffer A, and this was applied to a Q Sepharose (Sigma, St. Louis, Mo.) column (2.5×15 cm, 75 ml), previously equilibrated with buffer A. The column was washed with two column volumes of buffer A at a flow rate of 50 ml/hour. A gradient from zero to 500 mM NaCl in buffer A was then applied to the column over 750 ml. At this stage, 3 peaks of activity were seen (FIG. 1*a*). The first (peak I) was present in the flow through and had activity against MeOSuc-Ala-Ala-Pro-Val-pNA (SEQ ID NO:8). Peak II also had activity on this substrate but was present in fractions eluted by the salt gradient. Peak III, also eluted in the salt gradient, had activity against N-Suc-Ala-Ala-Pro-Phe-pNA (SEQ ID NO:7).

Peak I, whose activity was designated E1, was pooled, concentrated by ultrafiltration to 10 ml, using a 3K membrane (Filtron, North Boroush, Mass.), and applied to a Mono S FPLC column HR 5/5 (Pharmacia LKB Biotechnology Inc., Piscataway, N.J.), previously equilibrated with buffer A. The column was first washed with 5 column volumes of buffer A at 1.0 ml/minute, followed by a gradient from zero to 500 mM NaCl in buffer A, to elute bound proteins. Fractions of 1 ml were collected and assayed for amidolytic activity against MeOSuc-Ala-Ala-Pro-Val-pNA (SEQ ID NO:8). Those with this amidolytic activity were then applied to and separated on a Superdex 75 gel filtration column HR 10/30 (Pharmacia LKB Biotechnology Inc.), previously equilibrated with 150 mM NaCl in buffer A. Active fractions were pooled and used for further analysis.

Figure 1B:
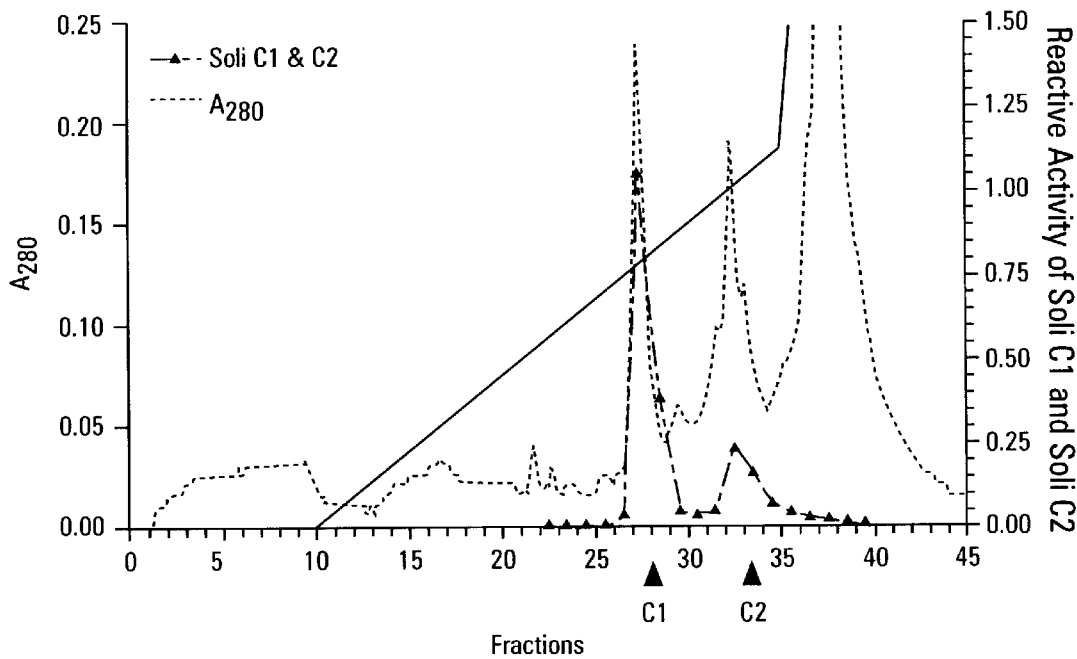

The purification of the enzymes present in peaks II and III were essentially identical. Fractions from each peak were pooled, dialyzed (MWCO 3,500, Spectrum, Laguna Hills, Calif.) for 4 hours at 4° C. against buffer A, and concentrated to 10 ml by ultrafiltration, using a 3K membrane (Filtron). These samples were then separately applied to a Mono Q FPLC column HR 5/5 (Pharmacia LKB Biotechnology Inc.), previously equilibrated with buffer A, and the column then washed with 5 column volumes of buffer A. Bound proteins were eluted with a gradient from zero to 500 mM NaCl in buffer A. All fractions were assayed for amidolytic activity against either MeOSuc-Ala-Ala-Pro-Val-pNA (SEQ ID NO:8) (peak II) or Suc-Ala-Ala-Pro-Phe-pNA (SEQ ID NO:7) (peak III), as described above. The enhanced resolution offered by Mono Q separated the activity in peak III into two separate proteins both of which hydrolyzed Suc-Ala-Ala-Pro-Phe-pNA (FIG. 1*b*). These are, therefore, referred to as C1 and C2, while a single activity was recovered from peak II (E2). All active fractions from this purification step were individually pooled and concentrated to 0.5 ml, by ultrafiltration, using a Filtron 3K Microsep (Filtron). For final purification each concentrated fraction was loaded onto and eluted from a Superdex 75 gel filtration column HR 10/30, previously equilibrated with buffer A. Active fractions were pooled and used for further analysis. Purification of S. invicta 4th instar larvae proteinases is shown in Table I.

concentrations ranging from 10 nM to 5 mM, with the final concentration of each enzyme being 10 nM in the specific optimum buffers utilized. $V_{max}$ and $K_m$ values were measured by using the computer program Hyperbolic Regression Analysis (J. A. Easterby, University of Liverpool, United Kingdom).

IEF—Isoelectrofocusing of the purified proteinases was performed on precast isoelectric focusing gels (pH 3–10) obtained under the trade designation SERVALYT PRE-

TABLE I

Purification of *Solenopsis invicta* 4th instar larvae proteinases.

| Proteinase | Fraction step | Total activity [a] units | Total protein [b] mg | Specific activity units/mg | Purification -fold | Yield [c] % |
|---|---|---|---|---|---|---|
| Soli E1 | Crude extract | 26,100 | 186 | 140 | 1 | 100 |
| | Acetone precipitation | 23,700 | 110 | 215 | 1.5 | 91 |
| | Peak I from Q Sepharose | 10,900 | 41.5 | 260 | 1.8 | 42 |
| | Mono S, FPLC | 6,840 | 0.586 | 11,700 | 84 | 26 |
| Soli E2 | Crude extract | 26,100 | 186 | 140 | 1 | 100 |
| | Acetone precipitation | 23,700 | 110 | 215 | 1.5 | 91 |
| | Peak II from Q Sepharose | 9,380 | 22.7 | 410 | 2.9 | 35 |
| | Mono Q, FPLC | 4,190 | 0.859 | 4,900 | 35 | 16 |
| | Superdex 75, FPLC | 1,500 | 0.132 | 11,400 | 81 | 6 |
| Soli C1 | Crude extract | 41,600 | 186 | 220 | 1 | 100 |
| | Acetone Precipitation | 38,700 | 110 | 350 | 1.6 | 93 |
| | Peak III from Q Sepharose | 19,400 | 6.4 | 3,030 | 13.8 | 47 |
| | Mono Q, FPLC | 11,700 | 0.725 | 16,100 | 73 | 28 |
| Soli C2 | Crude extract | 41,600 | 186 | 220 | 1 | 100 |
| | Acetone precipitation | 38,700 | 110 | 350 | 1.6 | 93 |
| | Peak III from Q Sepharose | 19,400 | 6.4 | 3,030 | 13.8 | 47 |
| | Mono Q, FPLC | 1,010 | 0.130 | 7,770 | 35.3 | 2.4 |
| | Superdex 75, FPLC | 720 | 0.030 | 24,000 | 109 | 1.7 |

[a] Based on enzymatic activity using MeOSuc-Ala-Ala-Pro-Val-pNA (SEQ ID NO:8) or Suc-Ala-Ala-Pro-Phe-pNA (SEQ ID NO:7), where 1 unit = 1 nmol of pNA released per minute
[b] 3 grams of larvae extracted.
[c] Based on initial activity in crude extract.

Enzyme Assay—Generally, the amidolytic activities of each proteinase were measured with the substrates MeOSuc-Ala-Ala-Pro-Val-pNA (SEQ ID NO:8) and N-Suc-Ala-Ala-Pro-Phe-pNA (SEQ ID NO:7) in 0.05 M Tris-HCl and 100 mM NaCl pH 7.4 (assay buffer). Release of the pNA group was assayed by monitoring the optical density of the test solution at 404 nM. Enzyme inhibition assays by protein inhibitors were conducted in the same assay buffer using an inhibitor concentration ranging from 0.02–50 nM with a 10 minute preincubation time and with the final enzyme concentration being 1.0 nM. All kinetic studies with substrates and inhibitors were performed at the optimum pH of the individual proteinases, utilizing the following buffers: 150 mM NaCl, 50 mM Tris-HCl pH 8.0 (E1); 150 mM NaCl, 50 mM CHES pH 9.5 (E2 and C2); and 150 mM NaCl, 50 mM CAPS pH 10.0 (C1).

Sodium Dodecyl Sulfate Polyacrylamide Gel Electrophoresis (SDS-PAGE)—The SDS-PAGE method devised by H. Schagger et al. (*Anal. Biochem.* 166, 368–379 (1987)), using a Tris-HCl/Tricine buffer system, was used throughout this study.

pH analysis—The determination of pH optimum and stability for each enzyme was performed using a Universal Phosphate Buffer system, which is a buffer made from boric acid and phosphoric acid titrated with sodium hydroxide such that the ionic strength is the same at any pH. Briefly, equal volumes of a solution of 80 mM boric acid and a solution of 80 mM phosphoric acid were combined, and 200 mM sodium hydroxide was added to bring the mixture to the desired pH.

Enzyme Kinetics and Specificity—$V_{max}$ and $K_m$ values were determined using substrates or synthetic inhibitors at COTES (Cresent Chemical Co., Inc., Hauppauge, N.Y.). Sample preparations and isoelectrofocusing were carried out following instructions provided by Pharmacia and using the Pharmacia Flatbed Electrophoresis Unit.

Sequence analysis—Purified proteins were subjected to SDS-PAGE and electroblotted on polyvinylidene difluoride membranes using 10 mM CAPS pH 11, 10% methanol (P. Matsudaira, *J. Biol. Chem.* 262, 10035–10038 (1987)). The membrane was washed thoroughly with water and stained with Coomassie Blue G250. The blot was air-dried and the bands containing enzymes were cut out and subjected to N-terminal sequence analysis with an Applied Biosystems Procise Protein Sequencer (Foster City, Calif.) using the program designed by the manufacturer.

Results

Enzyme purification—Acetone precipitation proved to be an excellent first step, as opposed to ammonium sulfate or acid precipitation. Both ammonium sulfate or acid precipitation caused drastic losses of all enzymatic activities. Indeed, the use of acetone effectively removed 40% of the unwanted proteins from the crude extract, while it had little negative effect on the activity of Soli C and limited loss of activity for both Soli E1 and Soli E2 (10–20%). Significantly, the use of Q Sepharose as a second step then separated the four enzymes into three peak fractions, with Soli E1, which failed to bind to Q Sepharose, being readily purified by the use of Mono S (FIG. 1*a*). The sample from this step was 98% pure. Minor bands were seen only when the sample was well overloaded on an SDS-PAGE gel. Therefore, gel filtration chromatography was utilized to obtain >99% purity.

Anion-exchange chromatography on Mono Q increased the specific activity of Soli E2 about 12 fold and, more significantly, separated Soli C1 and Soli C2 into distinct activities (FIG. 1b). After Mono Q, the level of purity for both Soli E2 and Soli C2 was only near 65% while Soli C1 was judged to be 90% pure. Thus, gel filtration was again utilized which again achieved 99% purity for Soli E2, Soli C1, and Soli C2.

SDS-PAGE analysis—SDS-PAGE of all four purified enzymes gave single bands with molecular weights of 23, 24, 25 and 28 kDa respectively for Soli E1, Soli E2, Soli C1, and Soli C2. A duplicate gel in which all of the samples were treated with $^3$H-DFP was exposed to x-ray film. The radiolabeled proteins confirmed that the purified products were the target enzymes for this serine proteinase inhibitor.

Enzyme specificity—The testing of numerous synthetic para-nitroanilide substrates against each of the four isolated proteinases supported the hypothesis that two were chymotrypsin-related in specificity (i.e., Soli C1 and Soli C2) while two had activities indicative of a relationship to pancreatic elastase (i.e., Soli E1 and Soli E2) (table II). Both Soli C1 and Soli C2 were broadly specific, in that they readily hydrolyzed substrates with P1 Leu and Phe residues, while Soli E1 and Soli E2 had narrow specificity towards P1 Ala or Val, with Soli E2 being particularly more active with the latter amino acid residue. However, the activity of each of the four enzymes was also affected by residues in the P2 to P4 positions of the substrates tested. Soli C1 favored a hydrophobic residue in the P2 position of the substrate but worked well on substrates which possessed proline in the P2 position. For Soli C2, the amino acid residue in the P3 position did not appear to effect activity, however a charged residue in the P4 position decreased activity.

TABLE II

Amidolytic activity of S. invicta proteinases

| Substrate | Vmax/Km | | | | SEQ ID NO: |
|---|---|---|---|---|---|
| | C1 | C2 | E1 | E2 | |
| Suc-Ala-Phe-Leu-pNA | 84 | <1 | <1 | <1 | |
| MeOSuc-Ala-Pro-Leu-pNA | 56 | <1 | <1 | <1 | |
| Suc-Ala-Ala-Phe-pNA | 362 | <1 | <1 | <1 | |
| Suc-Phe-Leu-Phe-pNA | 1348 | 96 | <1 | <1 | |
| Suc-Gln-Pro-Phe-pNA | 1051 | <1 | <1 | <1 | |
| Suc-Leu-Pro-Phe-pNA | 338 | <1 | <1 | <1 | |
| Suc-Phe-Pro-Phe-pNA | 612 | 27 | <1 | <1 | |
| Suc-Phe-Val-Phe-pNA | 779 | 29 | <1 | <1 | |
| Suc-Ala-Pro-Ala-pNA | <1 | <1 | 121 | 34 | |
| Suc-Ala-Ala-Val-Ala-pNA | <1 | <1 | 112 | 52 | 9 |
| Suc-Ala-Ala-Pro-Leu-pNA | 40 | 59 | <1 | <1 | 10 |
| Suc-Ala-Ala-Pro-Met-pNA | 25 | 179 | <1 | <1 | 11 |
| Suc-Phe-Ala-Ala-Phe-pNA | 438 | 280 | <1 | <1 | 12 |
| Suc-Ala-Ala-Pro-Phe-pNA | 1125 | 630 | <1 | <1 | 7 |
| Suc-Ala-Leu-Pro-Phe-pNA | 270 | 301 | <1 | <1 | 13 |
| Suc-Ala-Phe-Pro-Phe-pNA | 621 | 582 | <1 | <1 | 14 |
| Suc-Glu-Val-Pro-Phe-pNA | 239 | 52 | <1 | <1 | 15 |
| Suc-Leu-Val-Pro-Phe-pNA | 204 | 1099 | <1 | <1 | 16 |
| Suc-Met-Val-Pro-Phe-pNA | 790 | 1271 | <1 | <1 | 17 |
| Suc-Phe-Val-Pro-Phe-pNA | 381 | 138 | <1 | <1 | 18 |
| HCl-Ile-His-t-Pro-Phe-pNA | 722 | 558 | <1 | <1 | 19 |
| MeOSuc-Ala-Ala-Pro-Val-pNA | <1 | <1 | 11 | 127 | 8 |

The assay was performed at 25° C. in 20% Me$_2$SO, optimum buffer for each enzyme.
$^1$t = tosyl (CH$_3$C$_6$H$_4$SO$_2$-).

Inhibition profile—In accordance with the fact that all four enzymes were serine proteinases, each was readily inhibited by DFP but not by other class-specific proteinase inhibitors, including E-64, EDTA and Pepstatin. Nevertheless, the serine proteinase inhibitor, 3,4-dichloroisocoumarin, only inhibited Soli E1 and Soli E2 but not Soli C1 or Soli C2, except after long incubation periods.

Testing of synthetic inhibitors including coumarins, peptidyl chloromethyl ketones and organophosphates (Table III) gave results which were in parallel with substrate specificities as described above. Those inhibitors with P1-Phe residues inhibited Soli C1 and Soli C2 most efficiently while those possessing P1-Val were most effective on Soli E1 and Soli E2. Significantly, the activities on the proteases on synthetic substrates was paralleled by the specificity of the various synthetic inhibitors tested. Indeed, the best chloromethyl ketone against Soli C1 (Z-Gly-Leu-Phe-CK), was similar to the most suitable substrate. In contrast, the organophosphates inhibited the proteases better, possibly due to the negative charge of these molecules.

TABLE III

Effect of peptide inhibitors on the amidolytic activity of S. invicta

| | Max Inhibition Rate/IC$_{50}$$^1$ | | | | SEQ ID NO: |
|---|---|---|---|---|---|
| | C1 | C2 | E1 | E2 | |
| TLCK | <0.10 | <0.10 | <0.10 | <0.10 | |
| TPCK | 2.35 | 0.80 | <0.10 | <0.10 | |
| Z-Ala-CK$^2$ | 0.57 | <0.10 | <0.10 | <0.10 | |
| Z-Phe-CK | 3.78 | 1.31 | <0.10 | <0.10 | |
| Z-Trp-CK | 0.67 | <0.10 | <0.10 | <0.10 | |
| Ac-Ala-Leu-CK$^3$ | 0.58 | <0.10 | <0.10 | <0.10 | |
| Ac-Gly-Phe-CK | 0.95 | <0.10 | <0.10 | <0.10 | |
| Ac-Leu-Phe-CK | 8.50 | 0.43 | <0.10 | <0.10 | |
| IsoVal-Phe-CK$^4$ | 7.69 | 0.93 | 0.48 | 0.53 | |
| Ac-Val-Phe-CK | 0.73 | <0.10 | <0.10 | <0.10 | |
| Z-Gly-Leu-Ala-CK | 0.38 | <0.10 | 0.40 | <0.10 | |
| Ac-Ala-Pro-Ala-CK | <0.10 | <0.10 | 0.71 | <0.10 | |
| Z-Gly-Gly-Phe-CK | 2.16 | 0.18 | <0.10 | <0.10 | |
| Z-Gly-Leu-Phe-CK | 44.51 | 3.19 | <0.10 | <0.10 | |
| Ac-Ala-Ala-Ala-Ala-CK | <0.10 | <0.10 | 0.23 | <0.10 | 20 |
| Ac-Ala-Ala-Phe-Ala-CK | <0.10 | <0.10 | 0.18 | 0.27 | 21 |
| Ac-Ala-Ala-Pro-Ala-CK | <0.10 | <0.10 | 1.46 | 0.68 | 22 |
| Ac-Ala-Ala-Pro-Ile-CK | <0.10 | <0.10 | 0.19 | 24.97 | 23 |
| MeOsuc-Ala-Ala-Pro-Val-CK | <0.10 | <0.10 | 0.61 | 32.59 | 24 |
| Z-Phe-$^P$(OPh)$_2$$^5$ | 29.41 | 94.89 | <0.10 | <0.10 | |
| Z-Phe-Phe-$^P$(OPh)$_2$ | 246.67 | 266.09 | <0.10 | <0.10 | |
| Z-Leu-Phe-$^P$(OPh)$_2$ | 150.69 | 198.86 | <0.10 | <0.10 | |
| Z-Phe-Leu-Phe-$^P$(OPh)$_2$ | 1116.80 | 3694.80 | <0.10 | <0.10 | |
| Z-Val-$^P$(OPh)$_2$ | <0.10 | 0.37 | 2.24 | 6.36 | |
| Z-Ala-Val-$^P$(OPh)$_2$ | <0.10 | 0.21 | 1.41 | 27.23 | |
| Z-Pro-Val-$^P$(OPh)$_2$ | 0.11 | 0.23 | 1.17 | 36.57 | |
| Z-Val-Val-$^P$(OPh)$_2$ | 1.21 | 4.77 | 25.93 | 76.81 | |
| Boc-Ala-Pro-Val-$^P$(OPh)$_2$ | 0.71 | 0.78 | 395.91 | 665.86 | |
| Boc-Val-Pro Val-$^P$(OPh)$_2$ | 6.80 | 2.29 | 790.05 | 735.43 | |
| DCIC$^6$ | 0.24 | 0.70 | 3.77 | 32.42 | |

Results are for 10 minutes incubation at 25° C., 10% Me$_2$SO, optimum buffer for each enzyme.
$^1$IC$_{50}$ = the concentration at which 50% of the enzyme is inhibited
$^2$CK = chloromethyl ketone
$^3$Ac = acetyl
$^4$IsoVal = Iso-valine
$^5$$^P$(OPh)$_2$ = organophosphate
$^6$DCIC = dichloro iso-coumarin Testing of naturally occurring protein inhibitors of serine proteinases on the four enzymes further substantiated the specificities of the two pairs of proteinases (table IV), with members of the ovomucoid family being particularly specific towards Soli E1 and Soli E2 but showing no activity against Soli C1 or Soli C2. In contrast, Trasylol was only active against Soli C1 and LBTI against Soli C1 and Soli C2. All other inhibitors examined were generally inhibitory towards all four enzymes.

TABLE IV

Effect of Naturally Occurring Protease Inhibitors on
the amidolytic activity of *S. invicta*

IC$_{50}$ (nM)

| Inhibitor | Soli C1 | Soli C2 | Soli E1 | Soli E2 |
|---|---|---|---|---|
| Canadian Goose OM | NI[a] | NI | 0.137 | 7.680 |
| Canadian Goose OM Domain III | NI | NI | 1.511 | 27.283 |
| Domestic Goose OM | NI | NI | 1.642 | 6.026 |
| Domestic Goose OM Domain III | NI | NI | NI | 5.579 |
| Eglin C | 1.240 | 0.442 | 3.929 | 1.891 |
| Trasylol | 5.967 | NI | NI | NI |
| Soy Bean Trypsin Inhibitor I-S | 36.985 | 1.410 | 4.218 | 5.575 |
| Lima Bean Trypsin Inhibitor | 18.353 | 1.460 | NI | NI |
| α1-PI | 0.338 | 0.271 | 1.198 | 0.604 |
| Potato Inhibitor I | 2.628 | 1.480 | 12.120 | 9.132 |
| Potato Inhibitor II | 14.138 | 1.105 | 29.658 | 10.122 |

Results are for 10 minutes incubation at 25° C. in 50 mM Tris-HCl, 100 mM NaCl, pH 7.4.
[a]NI, no inhibition or IC$_{50}$ > 50 nM.

pH Optimum—The pH optimum for each enzyme, as determined by plotting the V$_{max}$ of substrate hydrolysis, at room temperature, in a pH range from 3.0 to 12.0, gave values of 8.0 for Soli E1, 8.5–10 for Soli E2, from 9.0–10.5 for Soli C1, and 9.0 for Soli C2.

Stability—Soli C1 was found to be stable for several days between the pH range 7–9 at 37° C. Soli C2, Soli E1 and Soli E2 on the other hand, lost their activities fairly quickly over all pHs but were most stable at pH 8.0, 7.0 and 8.5, respectively.

IEF—Based on Serva Test Mix 9 IEF standards (Cresent Chemical Co., Inc.), the proteinases migrated to the following pI's; Soli E1, 10.0; Soli E2 (3 isoforms), 6.9, 8.3, 8.5; Soli C1, 4.7; and Soli C2, 4.2.

N-terminal sequence analysis—The N-terminal sequences of the enzymes indicated some degree of conservation between the enzymes, especially with regard to an Ile-Val-Gly-Gly- consensus sequence (SEQ ID NO:31) at the amino terminus, which is also highly conserved in most serine proteinases. Aside from these first four residues, all four enzymes proved to be novel in that they shared no significant identity with each other or with other proteinases, at least in the first 20 amino acid residues when compared in Genebank (Table V).

Enzyme activity in developing stages of *S. invicta*—As shown in table VI, extracts of each stage of larval development showed only limited production of the two enzyme forms until the 4th instar larvae stage. Significantly, no activity was present in subsequent stages of development, supporting the hypothesis that the 4th instar larvae played major roles in the digestion and distribution of food and food products, respectively, to other larvae and to the adult insects. It is also possible that some of the early larval stages, which apparently contained some enzyme activity, may have been contaminated with the 4th instar larvae during separation of the various developing forms.

TABLE VI

Amidolytic activity of developmental stages of *S. invicta*

| | Chymotripsin-like activity* | Elastase-like activity* |
|---|---|---|
| Egg | 0 | 0 |
| 1$^{st}$ Instar | 24 | 12 |
| 2$^{nd}$ Instar | 27 | 13 |
| 3$^{rd}$ Instar | 36 | 43 |
| 4$^{th}$ Instar | 100 | 100 |
| Prepupae | 0 | 0 |
| Pupae | 0 | 0 |
| Adult | 0 | 0 |

Assay was performed at 25° C. in 50 mM Tris-HCl, 100 mM NaCl, pH 7.4.
*percent activity relative to that found in 4$^{th}$ instar larvae.

Example 2

Molecular Cloning of Soli E2

Materials and Methods

Polynucleotide kinase, T4 DNA ligase, T4 polymerase, DNA polymerase I, Klenow enzyme and random priming kit were purchased from Boehringer (Mannheim, Germany). Restriction enzymes were from New England Biolabs, Inc. (Beverly, Mass.). HYBOND-N membranes, [α-$^{32}$P]dATP and [γ-$^{32}$P]ATP were obtained from Amersham Life Science, Inc. (Arlington Heights, Ill.). The T7 DNA polymerase sequencing kit was bought from United States Biochemical (Cleveland, Ohio).

RNA Preparation and Northern Blot Analysis—Total RNA was prepared from developmental stages using guanidinium thiocyanate (GTC) extraction, followed by centrifugation through a CsCl gradient (V. Glisen et al. *Biochem.* 13 2633–2637 (1974); A. Ullrich et al. *Science,* 196, 1313–1319 (1977)). Briefly, about 200 μl of cells were lysed

TABLE V

Amino-terminal sequence of *S. invicta* 4th instar larvae proteinases

Soli C1[1]- Ile-Val-Gly-Gly-Asp-Ala-Pro-Val-Gly-Lys-Tyr-Pro-Tyr-Gln-Val-Ser-Leu-Arg-Leu-Ser-Gly- Soli C2[2]- Ile-Val-Gly-Gly-Glu-Pro-Ala-Pro-Gly-Gly-Ala-Tyr-Pro-Phe-Ile=Val-Ser-Leu-Gln-Val- Soli E1[3]- Ile-Val-Gly-Gly-Gln-Pro-Ala-Thr-Pro-Gly-Glu-Phe-Pro-His-Gln-Gly-Ser-Leu-Arg-Val- Soli E2[4]- Ile-Val-Gly-Gly-Gln-Asp-Ala-Ala-Pro-Gly-Glu-Phe-Pro-His-Gln-Gly-Ser-Leu-Arg-Leu-Arg- -
                Gly-Ser-His-Ile-

[1]: SEQ ID NO:25
[2]: SEQ ID NO:26
[3]: SEQ ID NO:27
[4]: SEQ ID NO:28 in 1.5 ml of GTC homogenization buffer (4.0 M guanidinium thiocyanate, 0.1 M Tris, pH 7.5, and 1% 2-mercaptoethanol), the DNA sheared with a needle, and solution layered onto a cushion of 5.7 M CsCl and 0.01 M EDTA, pH 7.5 in a centrifuge tube. After centrifugation at 3,600 RPM for 12 hours, the supernatant was removed and the pellet suspended in 400 μl of 0.1% diethyl pyrocarbonate.

Isolated RNA (5 μg) was heated to 65° C. for 10 min in a solution containing 50% formamide 20 mM 3-[N-morpholino] propanesulfonic acid (MOPS), 5 mM sodium acetate, 1 mM EDTA, and 2.2 M formaldehyde prior to electrophoresis in 1% agarose, containing the same buffer, at 35 volts overnight. The separated RNA was transferred to a HYBOND-N membrane according to the manufacturer's instructions. Membranes were prehybridized at 47° C. or 65° C. for testing against degenerate oligonucleotide and cDNA probes, respectively, for 3 hours in 10% dextran sulfate, 1 M NaCl and 1% SDS. The probes were made by Molecular Genetics Facility (University of Georgia). Hybridization was carried out in the same solution, with either a degenerate oligonucleotide probe labeled at the 5' end using polynucleotide kinase and [γ-$^{32}$P]ATP (Sambrook et al., Molecular Cloning, A Laboratory Manual, 2nd edition, Cold Spring Harbor Laboratory Press (1989)) or with a cDNA clone labeled by random priming (A. Feinberg et al. *Anal. Biochem.* 132, 6–13 (1983)). After overnight hybridization at either 47° C. for the degenerate oligonucleotide probe or 65° C. for the cDNA clone, the filters were washed twice with 2 x SSC (1 x SSC: 150 mM NaCl, 15 mM sodium citrate pH 7.0) for 20 min at room temperature and then twice with 2 x SSC, 1% SDS for 20 minutes, again at 45° C. for the degenerate oligonucleotide probe or at 63° C. for the cDNA clone, before being exposed to x-ray film.

Production and Screening of the cDNA Library—Poly (A)$^+$RNA was isolated from total 4th instar larvae RNA using the Poly(A) Quik mRNA Isolation Kit (Stratagene, La Jolla, Calif.), and was used to create a λgt10 library using the cDNA Synthesis kit, ZAP-cDNA Synthesis kit and cDNA Gigapack II Gold Cloning kit (Stratagene) according to the manufacturer's instructions. Briefly, 5 μg of Poly(A)$^+$RNA primed with oligo dT-Xho I primer GAGAGAGAGAGAGAGAGAGAAC-TAGTCTCTGAGTTTTTTTTTTTTTTTTT T (SEQ ID NO:33) (2.8 μg) in 50 mM Tris-HCl, 7 mM MgCl, pH 7.5, and 0.5 mM each of dATP, dTTP, dCTP, and dGTP, was used for the first strand synthesis. The material obtained was treated with RNAase H, and the second strand was synthesized using DNA polymerase I (U. Gubler et al. *Gene* 25, 263–269 (1983)). First and second strand synthesis was monitored by incorporation of [α-$^{32}$P]dATP. The double stranded DNA was blunt ended using recombinant Pfu polymerase (Sambrook et al., Molecular Cloning, A Laboratory Manual, 2nd edition, Cold Spring Harbor Laboratory Press (1989)). Following phenol extraction and ethanol precipitation as described in Sambrook et al. (Molecular Cloning, A Laboratory Manual, 2nd edition, Cold Spring Harbor Laboratory Press (1989)), the cDNA was ligated into EcoR I adaptors and purified using a sephacryl S-400 column (Sambrook et al., Molecular Cloning, A Laboratory Manual, 2nd edition, Cold Spring Harbor Laboratory Press (1989)). The cDNA was then ligated into EcoR I cleaved λgt10 DNA and packaged in vitro into NM514 as described in Sambrook et al. (Molecular Cloning, A Laboratory Manual, 2nd edition, Cold Spring Harbor Laboratory Press (1989)). λgt10 containing the cDNA library was propagated and transferred to nitrocellulose membranes as suggested by the manufacturer. Screening of the cDNA library was performed with the following degenerate oligonucleotide probe which covered the region from Gly-10 to Gly-16 in the N-terminal sequence of the mature protein: CCYTGATGIG-GRAAYTCNCC (SEQ ID NO:30). The oligonucleotide probe was labeled at the 5' end using polynucleotide kinase and [γ-$^{32}$P]ATP. Screening was carried out in 5 x Denhardt's solution (5 x Denhardt's is 1% Ficoll, 1% polyvinylpyrolidone, 1% BSA), 0.12 M phosphate buffer, pH 6.8, and 3 x SSC at 47° C. for about 12 hours. Hybridized membranes were washed twice in a solution of 1 x SSC and 0.1% SDS for 20 minutes, and then washed twice with a solution containing 1 x SSC for 20 minutes. The washes were done at 42° C.

DNA Subcloning and Nucleotide Sequencing—EcoR I digested DNA inserts from recombinant phages were subcloned into the plasmid pUC19, using standard techniques (Sambrook et al., Molecular Cloning, A Laboratory Manual, 2nd edition, Cold Spring Harbor Laboratory Press (1989)). Sequencing was performed using a T7 DNA polymerase sequencing kit (United States Biochemical) and/or from plasmid DNA by the Molecular Genetics Facility (University of Georgia core facility, Athens, Ga.).

Computer Assisted Analysis of Sequence Data—The sequence of Soli E2 was compared with all entries in the OWL database (A. J. Bleasby et al. *Protein Engineering*, 3 153–159 (1990)) using TFASTA and LALIGN on-line database search programs.

Results

Isolation of mRNA from Fire Ant Larvae—Fire ant larvae possess several proteinases, one of which is referred to as Soli E2, a 24 kDa proteinase which cleaves peptide bonds after hydrophobic residues, especially Val (S. T. Whitworth et al. *J. Biol. Chem.*, 273, 14430–14434 (1998)). A degenerate oligonucleotide probe based on the N-terminal amino acid sequence of Soli E2 was designed to clone and sequence the cDNA encoding Soli E2. The probe was used to analyze total, Poly(A)$^-$ and Poly(A)$^+$ RNA from *S. invicta* 4$^{th}$ instar larvae. A Northern blot analysis showed that Soli E2 mRNA was present in the 4th instar larvae with an estimated size of the transcript being 1400 base pairs.

Construction and Screening of the Library—Having shown that fire ant larvae do indeed express mRNA for Soli E2, an oligo(dT)-primed cDNA library from the Poly(A)$^+$ RNA of the 4th instar larvae was constructed in λgt10. The library obtained contained approximately 1.46×10$^6$ independent clones. Screening of 25,000 phages with the degenerate oligonucleotide probe resulted in the detection of two positive clones, both of which (pSE2-1 and pSE2-2; FIG. 2b) were analyzed in detail, as described below.

Nucleotide and Amino Acid Sequence of Soli E2—As shown in FIG. 3, pSE2-2 cDNA was found to contain a 1362 base pair insert with a 747 base pair open reading frame extending from an ATG start codon at nucleotide 450 to a TAA stop codon at nucleotide 1199. This ORF was based on the criteria that the in-frame ATG triplet was found at this position and the in-frame sequence of nucleotides 519 to 581 matched the N-terminal amino acid sequence obtained from Edman degradation of the purified proteinase. The ORF encoded a putative zymogen (i.e., a protease that must be cleaved before it has amidolytic activity) of 249 amino acids, which was cleaved to a mature form of 226 residues in the secreted proteinase having a calculated molecular mass of 24.6 kDa. Sequencing of the pSE2-1 clone revealed a 893 bp insert with an ORF starting at nucleotide 6. This clone was identical to nucleotides 445 to 1337 of pSE2-2 and differed only in that it lacked the 5' untranslated region.

Soli E2 appears to be cleaved after lys (−1) to yield the mature form of 226 residues (see FIG. 3). This was supported by the following data: (i) the N-terminal sequence of the purified proteinase revealed the conserved IVGG (SEQ ID NO:31) sequence, common to serine proteases, 23 residues from the ATG start codon; (ii) the calculated $M_r$ of the 226 amino acid form (24.6 kDa) was in agreement with that obtained experimentally; and (iii) the putative signal and activation sequence, residues −1 to −23, possessed the typical hydrophobic N-terminal sequence followed by a region containing acidic amino acid residues, consistent with other known secreted proteinases, particularily trypsin (A. R. Khan et al. *Protein Sci.*, 7, 815–836 (1998)). Indeed, upstream from the activation site, this putative activation peptide sequence (EEPRK) (SEQ ID NO:32) resembled that of human and bovine trypsin (DDDDK) (SEQ ID NO:29) (M. Emi et al. *Gene*, 41, 305–310 (1986); O. Mikes et al. *Biochem. Biophys. Res. Commun.*, 24, 346–352 (1966)).

Sequence Similarities to Other Proteinases—Based on sequence data, Soli E2 shared sequence similarity to other members of the serine proteinase family from closely related and phylogenetically diverse species (FIG. 4), including such insect and mammalian proteinases as oriental hornet chymotrypsin II (37.8% identity, 65.8% similarity), fruit fly β trypsin (35.6% identity, 61.6% similarity), yellow fever mosquito trypsin 31A (35.2% identity, 59.2% similarity), and human leukocyte elastase (31.5% identity, 58.6% similarity). Comparing Soli E2 with these known proteinases, the active site triad was well conserved, particularly the regions surrounding residues His-57 and Ser-195 (chymotrypsin numbering system) (K. D. Jany et al. *Biochem Biophys. Acta.*, 668 197–200 (1981); K. D. Jany et al. *Biochem. Biophys. Res. Commun.*, 110, 1–9 (1983); S. Kalhok et al. *Insect Mol. Biol.*, 2, 71–79 (1993); and D. Farley et al. *Biol. Chem.*, 370, 733–747 (1989)). For Soli E2, other important amino acids, including Ala-178, Thr-197, Val-200 and Asp-209, were either conserved or replaced by chemically similar residues. The counterparts of these residues in HLE line the active site pocket and, therefore, confer primary specificity (W. Bode et al. *Biochem.*, 28, 1951–1963 (1989)), thus, supporting the suggestion that Soli E2 has catalytic activity similar to HLE. Furthermore, eight cysteine residues present at positions 26, 42, 124, 155, 169, 179, 189 and 203 of the mature protein were conserved, which suggests the formation of four disulfide bonds as also observed in HLE (W. Bode et al. *Embo. J.* 5, 2453–2458 (1986)).

Northern Blot Analysis of Developmental Stages—To determine the expression pattern of Soli E2, mRNA from all stages of development were analyzed by Northern blotting, using the full-length coding region (893 base pairs) pSE2-1 cDNA clone as a probe. 2-D spot densitometry of the gel showed that more than 86% of expressed Soli E2 was present in the 4th instar larvae, indicating that the *S. invicta* Soli E2 gene was primarily expressed in this larval stage. While there was evidence for the possibility of enzyme synthesis in the 3rd instar (12%) and, perhaps, also in the 2nd instar (<2%), the presence of Soli E2 mRNA in these stages may be due to contamination of 4th instar larvae, as a result of error in physical separation. This is likely the case since the size of the larvae at individual stages can vary (B. Holldobler et al. "The Ants," Harvard University Press, Cambridge (1990)), and there is not a definitive distinction between stages (R. S. Petralia et al. *Ann. Entomol. Soc. Am.* 72, 472–484 (1979)). Since other insects comprise a major portion of the fire ant's diet (D. J. Stradling et al. "Production Ecology of Ants and Termites," Cambridge University Press, New York, pp. 81–106 (1978)) and would require such a proteinase for the degradation of such exogenous sources of protein, the catalytic activity and pattern of expression fit the theory that Soli E2 is a digestive proteinase.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

| Sequence Listing Free Text | |
|---|---|
| SEQ ID NO:1 | Nucleotide sequence of cDNA. |
| SEQ ID NO:2 | Deduced amino acid sequence. |
| SEQ ID NO:3 | Deduced amino acid sequence. |
| SEQ ID NO:4 | Deduced amino acid sequence. |
| SEQ ID NO:5 | Deduced amino acid sequence. |
| SEQ ID NO:6 | Deduced amino acid sequence. |
| SEQ ID NO:7 | Synthetic para-nitroanilide substrate. The N' end cap is succinyl; the C' end cap is para-nitroanilide. |
| SEQ ID NO:8 | Synthetic para-nitroanilide substrate. The N' end cap is methoxy succinyl; the C' end cap is para-nitroanilide. |
| SEQ ID NO:9–18 | Synthetic para-nitroanilide substrate. The N' end cap is succinyl; the C' end cap is para-nitroanilide. |
| SEQ ID NO:19 | Synthetic para-nitroanilide substrate. The N' end cap is hydrogen chloride; the C' end cap is para-nitroanilide; amino acids 2 and 3 are linked by a tosyl group. |
| SEQ ID NOs:20–23 | Synthetic peptide inhibitor. The N' end cap is acetyl; the C' end cap is chloromethyl-ketone. |
| SEQ ID NO:24 | Synthetic peptide inhibitor. The N' end cap is methoxy succinyl; the C' end cap is chloromethyl-ketone. |
| SEQ ID NOs:25–28 | Amino terminal sequence. |
| SEQ ID NO:29 | Human and bovine trypsin activation peptide sequence. |
| SEQ ID NO:30 | Degenerate oligonucleotide probe. |
| SEQ ID NO:31 | Amino terminal sequence. |
| SEQ ID NO:32 | Putative activation peptide sequence. |
| SEQ ID NO:33 | Oligonucleotide primer. |

What is claimed is:

1. An isolated nucleic acid fragment encoding a polypeptide, wherein the nucleic acid fragment has a nucleotide sequence comprising nucleotides 519 to 1198 of SEQ ID NO:1, or a complement thereto.

2. A nucleic acid fragment having at least about 90% identity to nucleotides 519–1198 of SEQ ID NO:1, wherein the nucleic acid fragment encodes a polypeptide having elastase-like amidolytic activity.

3. A nucleic acid fragment having at least about 90% identity to nucleotides 519–1198 of SEQ ID NO:1, wherein the nucleic acid fragment encodes a polypeptide having elastase-like amidolytic activity for cleavage of a peptide bond present in a target polypeptide MeOSuc-Ala-Ala-Pro-Val-pNA (SEQ ID NO:8), and wherein the polypeptide and target polypeptide are in about 0.05 M Tris-HCl, about 100 mM NaCl at about pH 7.4 and about 25° C. for about 10 minutes.

* * * * *

SEQUENCE LISTING

<160> NUMBER OF SEQ ID NOS: 33

<210> SEQ ID NO 1
<211> LENGTH: 1361
<212> TYPE: DNA
<213> ORGANISM: Artificial Sequence
<220> FEATURE:
<223> OTHER INFORMATION: Description of Artificial Sequence: Nucleotide
      sequence of cDNA

<400> SEQUENCE: 1

```
gaataatcca ttcgtttatt ttatgatgga ttcctcccac aacggggccc t tgtatattt      60
tatacattcc agtgtataca aaatttctgg cggacgcttc tttaggtcta a agatatatg     120
cgccggatga cctattaacg aagacctcat tattaccctc tgctcctacg t agtaatgga    180
aggattgtac gacattcagg tctcgatcat tccactttat cattaagtta c catcagtgt    240
taacagatat attaaacatc tcattgctta tatagttggt tggttcagat t gttcaacta    300
cattttcctg cgccttttt ctaactacat aagctcgtac actgagcgga g gaatatagt    360
tagcacggaa gacgagctca ttttcgcat tgcttttct ccctgggatt t tctgaactt     420
catcggcacg agctcgtgcc gcattaacct gctaccattc attttcttag t ggtcggcgt    480
tcttgcacaa cagacgtttg ctgaggaacc cgagaagatc gtcggtggcc a agatgccgc    540
accaggcgaa tttccgcatc aaggttcctt gagattgcga ggctcacaca t tgtggctg     600
ctccatcatc ggcccgaaga caatcttgac tgccgctcat tgcgtggatg g tatcgcaga    660
atatccttat agtaacttca aggttgtgac cggcaccatc gatagatata c gggaggaga    720
gacccacgat gtgaagagcg ttcacgtgca tccgtattat tccgacagag t ggaagatgc    780
ttgggtgaat gatgttgcag tgatcacgct taaatcggcg attaagtaca a ccagtatca    840
aaaccgatt gccctggcca agacccgacc cgctgacgga acccaatgtc a attgtccgg    900
atggggtcag atcagcacga acggaccgct tccgcgcatt ctccaaaaga t gttccaggt    960
catatacaat caggaaaaat gcaagcaacg tcataatatg cctttaactg g cagtcacgt   1020
gtgcgcgtat aaccgctacg gaattggcgc ttgttccggt gacagcggtg g tccgctcat   1080
ctgcggtggc gtacagtgcg gtattacttc ctgggttctt ccttgcgcaa a gggtgagcc   1140
tgatgcctac accagtgtcg cttatcatta cgactttatt gaacaatatt t agaataaat   1200
ctatttgatg gtattgtcaa tggaaacaat ggatgtcaac gcgtcgaaag a atacgatgc   1260
gttggttacg ttttgaaaa agaagaatat acttctgtac ttacaatata a ataaataaa   1320
taaaacagtt ttagttaaat ctaaaaaaaa aaaaaaaaa a                          1361
```

<210> SEQ ID NO 2
<211> LENGTH: 249
<212> TYPE: PRT
<213> ORGANISM: Artificial Sequence
<220> FEATURE:
<223> OTHER INFORMATION: Description of Artificial Sequence: Deduced
      amino acid sequence

<400> SEQUENCE: 2

Met Leu Pro Phe Ile Phe Leu Val Val Gly V al Leu Ala Gln Gln Thr
 1               5                  10                  15

Phe Ala Glu Glu Pro Glu Lys Ile Val Gly G ly Gln Asp Ala Ala Pro
            20                  25                  30

Gly Glu Phe Pro His Gln Gly Ser Leu Arg L eu Arg Gly Ser His Ile

```
            35                  40                  45
Cys Gly Cys Ser Ile Ile Gly Pro Lys Thr Ile Leu Thr Ala Ala His
         50                  55                  60
Cys Val Asp Gly Ile Ala Glu Tyr Pro Tyr Ser Asn Phe Lys Val Val
 65                  70                  75                  80
Thr Gly Thr Ile Asp Arg Tyr Thr Gly Gly Glu Thr His Asp Val Lys
                 85                  90                  95
Ser Val His Val His Pro Tyr Tyr Ser Asp Arg Val Glu Asp Ala Trp
            100                 105                 110
Val Asn Asp Val Ala Val Ile Thr Leu Lys Ser Ala Ile Lys Tyr Asn
        115                 120                 125
Gln Tyr Gln Lys Pro Ile Ala Leu Ala Lys Thr Arg Pro Ala Asp Gly
130                 135                 140
Thr Gln Cys Gln Leu Ser Gly Trp Gly Gln Ile Ser Thr Asn Gly Pro
145                 150                 155                 160
Leu Pro Arg Ile Leu Gln Lys Met Phe Gln Val Ile Tyr Asn Gln Glu
                165                 170                 175
Lys Cys Lys Gln Arg His Asn Met Pro Leu Thr Gly Ser His Val Cys
            180                 185                 190
Ala Tyr Asn Arg Tyr Gly Ile Gly Ala Cys Ser Gly Asp Ser Gly Gly
        195                 200                 205
Pro Leu Ile Cys Gly Gly Val Gln Cys Gly Ile Thr Ser Trp Val Leu
    210                 215                 220
Pro Cys Ala Lys Gly Glu Pro Asp Ala Tyr Thr Ser Val Ala Tyr His
225                 230                 235                 240
Tyr Asp Phe Ile Glu Gln Tyr Leu Glu
                245

<210> SEQ ID NO 3
<211> LENGTH: 218
<212> TYPE: PRT
<213> ORGANISM: Artificial Sequence
<220> FEATURE:
<223> OTHER INFORMATION: Description of Artificial  Sequence: Deduced
      amino acid sequence

<400> SEQUENCE: 3

Ile Val Gly Gly Thr Asp Ala Pro Arg Gly Lys Tyr Pro Tyr Gln Val
 1               5                  10                  15
Ser Leu Arg Ala Pro Lys His Phe Cys Gly Gly Ser Ile Ser Lys Arg
            20                  25                  30
Tyr Val Leu Thr Ala Ala His Cys Leu Val Gly Lys Ser Lys His Gln
        35                  40                  45
Val Thr Val His Ala Gly Ser Val Leu Leu Asn Lys Glu Glu Ala Val
    50                  55                  60
Tyr Asn Ala Glu Glu Leu Ile Val Asn Lys Asn Tyr Asn Ser Ile Arg
 65                  70                  75                  80
Leu Ile Asn Asp Ile Gly Leu Ile Arg Val Ser Lys Asp Ile Ser Tyr
                 85                  90                  95
Thr Gln Leu Val Gln Pro Val Lys Leu Pro Val Ser Asn Thr Ile Lys
            100                 105                 110
Ala Gly Asp Pro Val Val Leu Thr Gly Trp Gly Arg Ile Tyr Val Asn
        115                 120                 125
Gly Pro Ile Pro Asn Asn Leu Gln Gln Ile Thr Leu Ser Ile Val Asn
    130                 135                 140
```

```
Gln Gln Thr Cys Lys Phe Lys His Trp Gly Leu Thr Asp Ser Gln Ile
145                 150                 155                 160

Cys Thr Phe Thr Lys Leu Gly Glu Gly Ala Cys Asp Gly Asp Ser Gly
                165                 170                 175

Gly Pro Leu Val Ala Asn Gly Val Gln Ile Gly Ile Val Ser Tyr Gly
                180                 185                 190

His Pro Cys Ala Val Gly Ser Pro Asn Val Phe Thr Arg Val Tyr Ser
            195                 200                 205

Phe Leu Asp Trp Ile Gln Lys Asn Gln Leu
            210                 215

<210> SEQ ID NO 4
<211> LENGTH: 253
<212> TYPE: PRT
<213> ORGANISM: Artificial Sequence
<220> FEATURE:
<223> OTHER INFORMATION: Description of Artificial  Sequence: Deduced
      amino acid sequence

<400> SEQUENCE: 4

Met Leu Lys Phe Val Ile Leu Leu Ser Ala Val Ala Cys Ala Leu Gly
1               5                   10                  15

Gly Thr Ile Pro Glu Gly Leu Leu Pro Gln Leu Asp Gly Arg Ile Val
                20                  25                  30

Gly Gly Thr Ala Thr Thr Ile Ser Ser Phe Pro Trp Gln Ile Ser Leu
            35                  40                  45

Gln Arg Ser Gly Ser His Ser Cys Gly Gly Ser Ile Tyr Thr Asp Arg
        50                  55                  60

Val Ile Val Thr Ala Ala His Cys Leu Gln Ser Val Ser Ala Ser Ser
65                  70                  75                  80

Leu Gln Ile Arg Ala Gly Ser Ser Tyr Trp Ser Ser Gly Gly Val Thr
                85                  90                  95

Val Lys Val Ser Ser Phe Lys Asn His Glu Gly Tyr Asn Pro Asn Thr
                100                 105                 110

Met Val Asn Asp Ile Ala Val Ile Arg Leu Ser Ser Ser Leu Gly Phe
            115                 120                 125

Ser Ser Thr Ile Lys Ser Ile Ser Leu Ala Ser Ser Asn Pro Ala Asn
        130                 135                 140

Gly Ala Ala Ser Val Ser Gly Trp Gly Thr Gln Ser Ser Gly Ser
145                 150                 155                 160

Ser Ser Ile Pro Ser Gln Leu Gln Tyr Val Asn Val Asn Ile Val Ser
                165                 170                 175

Gln Ser Lys Cys Ala Ser Ser Ala Tyr Gly Tyr Gly Ser Glu Ile Arg
            180                 185                 190

Asn Thr Met Ile Cys Ala Ala Ala Ser Gly Lys Asp Ala Cys Gln Gly
        195                 200                 205

Asp Ser Gly Gly Pro Leu Val Ser Gly Gly Val Leu Val Gly Val Val
    210                 215                 220

Ser Trp Gly Tyr Gly Cys Ala Tyr Ser Asn Tyr Pro Gly Val Tyr Ala
225                 230                 235                 240

Ser Val Ala Asp Leu Arg Ser Trp Val Ile Asn Asn Ala
                245                 250

<210> SEQ ID NO 5
<211> LENGTH: 254
<212> TYPE: PRT
<213> ORGANISM: Artificial Sequence
```

-continued

```
<220> FEATURE:
<223> OTHER INFORMATION: Description of Artificial  Sequence: Deduced
      amino acid sequence

<400> SEQUENCE: 5
```

Met Asn Gln Phe Leu Phe Val Ser Phe Cys Ala Leu Leu Asp Ser Ala
 1               5                  10                  15

Lys Val Ser Ala Ala Thr Leu Ser Ser Gly Arg Ile Val Gly Gly Phe
            20                  25                  30

Gln Ile Asp Ile Ala Glu Val Pro His Gln Val Ser Leu Gln Arg Ser
         35                  40                  45

Gly Arg His Phe Cys Gly Gly Ser Ile Ile Ser Pro Arg Trp Val Leu
     50                  55                  60

Thr Arg Ala His Cys Thr Thr Asn Thr Asp Pro Ala Ala Tyr Thr Ile
 65                  70                  75                  80

Arg Ala Gly Ser Thr Asp Arg Thr Asn Gly Gly Ile Ile Val Lys Val
                85                  90                  95

Lys Ser Val Ile Pro His Pro Gln Tyr Asn Gly Asp Thr Tyr Asn Tyr
            100                 105                 110

Asp Phe Ser Leu Leu Glu Leu Asp Glu Ser Ile Gly Phe Ser Arg Ser
        115                 120                 125

Ile Glu Ala Ile Ala Leu Pro Asp Ala Ser Glu Thr Val Ala Asp Gly
    130                 135                 140

Ala Met Cys Thr Val Ser Gly Trp Gly Asp Thr Lys Asn Val Phe Glu
145                 150                 155                 160

Met Asn Thr Leu Leu Arg Ala Val Asn Val Pro Ser Tyr Asn Gln Ala
                165                 170                 175

Glu Cys Ala Ala Ala Leu Val Asn Val Val Pro Val Thr Glu Gln Met
            180                 185                 190

Ile Cys Ala Gly Tyr Ala Ala Gly Gly Lys Asp Ser Cys Gln Gly Asp
        195                 200                 205

Ser Gly Gly Pro Leu Val Ser Gly Asp Lys Leu Val Gly Val Val Ser
    210                 215                 220

Trp Gly Lys Gly Cys Ala Leu Pro Asn Leu Pro Gly Val Tyr Ala Arg
225                 230                 235                 240

Val Ser Thr Val Arg Gln Trp Ile Arg Glu Val Ser Glu Val
                245                 250

```
<210> SEQ ID NO 6
<211> LENGTH: 271
<212> TYPE: PRT
<213> ORGANISM: Artificial Sequence
<220> FEATURE:
<223> OTHER INFORMATION: Description of Artificial  Sequence: Deduced
      amino acid sequence

<400> SEQUENCE: 6
```

Met Thr Leu Gly Arg Arg Leu Ala Cys Leu Phe Leu Ala Cys Val Leu
 1               5                  10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
         35                  40                  45

Leu Arg Gly Gly His Phe Cys Gly Ala Thr Leu Ile Ala Pro Asn Phe
     50                  55                  60

Val Met Ser Ala Ala His Met Thr Leu Gly Arg Arg Leu Ala Cys Leu
 65                  70                  75                  80

```
Phe Leu Ala Cys Val Leu Pro Ala Leu Leu Leu Gly Gly Thr Ala Leu
                 85                  90                  95

Ala Ser Glu Ile Val Gly Gly Arg Arg Ala Arg Pro His Ala Trp Pro
            100                 105                 110

Phe Met Val Ser Leu Gln Leu Arg Gly Gly His Phe Cys Gly Ala Thr
        115                 120                 125

Leu Ile Ala Pro Asn Phe Val Met Ser Ala Ala His Gln Leu Pro Ala
    130                 135                 140

Gln Gly Arg Arg Leu Gly Asn Gly Val Gln Cys Leu Ala Met Gly Trp
145                 150                 155                 160

Gly Leu Leu Gly Arg Asn Arg Gly Ile Ala Ser Val Leu Gln Glu Leu
                165                 170                 175

Asn Val Thr Val Val Thr Ser Leu Cys Arg Arg Ser Asn Val Cys Thr
            180                 185                 190

Leu Val Arg Gly Arg Gln Ala Gly Val Cys Phe Gly Asp Ser Gly Ser
        195                 200                 205

Pro Leu Val Cys Asn Gly Leu Ile His Gly Ile Ala Ser Phe Val Arg
    210                 215                 220

Gly Gly Cys Ala Ser Gly Leu Tyr Pro Asp Ala Phe Ala Pro Val Ala
225                 230                 235                 240

Gln Phe Val Asn Trp Ile Asp Ser Ile Ile Gln Arg Ser Glu Asp Asn
                245                 250                 255

Pro Cys Pro His Pro Arg Asp Pro Asp Pro Ala Ser Arg Thr His
            260                 265                 270

<210> SEQ ID NO 7
<211> LENGTH: 4
<212> TYPE: PRT
<213> ORGANISM: Artificial Sequence
<220> FEATURE:
<223> OTHER INFORMATION: Description of Artificial  Sequence: Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 7

Ala Ala Pro Phe
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial  Sequence: Synthetic
      para-nitroanalide substrate
<221> NAME/KEY: SITE
<222> LOCATION: (1)
<223> OTHER INFORMATION: methoxy succinyl end cap
<221> NAME/KEY: SITE
<222> LOCATION: (4)
<223> OTHER INFORMATION: para-nitroanalide end cap

<400> SEQUENCE: 8

Ala Ala Pro Val
  1

<210> SEQ ID NO 9
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 9

Ala Ala Val Ala
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 10

Ala Ala Pro Leu
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 11

Ala Ala Pro Met
  1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 12

Phe Ala Ala Phe
  1
```

```
<210> SEQ ID NO 13
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 13

Ala Leu Pro Phe
  1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 14

Ala Phe Pro Phe
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 15

Glu Val Pro Phe
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 16

Leu Val Pro Phe
  1
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalilde end ca p

<400> SEQUENCE: 17

Met Val Pro Phe
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: succinyl end cap
<221> NAME/KEY: SITE
<222> LOCATION: (4)
<223> OTHER INFORMATION: para-nitroanalide end cap

<400> SEQUENCE: 18

Phe Val Pro Phe
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial  Sequence:  Synthetic
      para-nitroanalide substrate
<221> NAME/KEY: SITE
<222> LOCATION: (1)
<223> OTHER INFORMATION: hydrogen chloride end cap
<221> NAME/KEY: SITE
<222> LOCATION: (2)..(3)
<223> OTHER INFORMATION: linked by a tosyl g roup
<221> NAME/KEY: SITE
<222> LOCATION: (4)
<223> OTHER INFORMATION: para-nitroanalide end cap

<400> SEQUENCE: 19

Ile His Pro Phe
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial  Sequence:  Synthetic
      peptide inhibitor
<221> NAME/KEY: SITE
<222> LOCATION: (1)
<223> OTHER INFORMATION: acetyl end cap
<221> NAME/KEY: SITE
<222> LOCATION: (4)
<223> OTHER INFORMATION: chloromethyl-ketone end c ap

<400> SEQUENCE: 20
```

Ala Ala Ala Ala
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide inhibitor
<221> NAME/KEY: SITE
<222> LOCATION: (1)
<223> OTHER INFORMATION: acetyl end cap
<221> NAME/KEY: SITE
<222> LOCATION: (4)
<223> OTHER INFORMATION: chloromethyl-ketone end c ap

<400> SEQUENCE: 21

Ala Ala Phe Ala
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide inhibitor
<221> NAME/KEY: SITE
<222> LOCATION: (1)
<223> OTHER INFORMATION: acetyl end cap
<221> NAME/KEY: SITE
<222> LOCATION: (4)
<223> OTHER INFORMATION: chloromethyl-ketone end c ap

<400> SEQUENCE: 22

Ala Ala Pro Ala
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide inhibitor
<221> NAME/KEY: SITE
<222> LOCATION: (1)
<223> OTHER INFORMATION: acetyl end cap
<221> NAME/KEY: SITE
<222> LOCATION: (4)
<223> OTHER INFORMATION: chloromethyl-ketone end c ap

<400> SEQUENCE: 23

Ala Ala Pro Ile
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide inhibitor
<221> NAME/KEY: SITE
<222> LOCATION: (1)
<223> OTHER INFORMATION: methoxy succinyl end c ap
<221> NAME/KEY: SITE
<222> LOCATION: (4)
<223> OTHER INFORMATION: chloromethyl-ketone end c ap -continued

```
<400> SEQUENCE: 24

Ala Ala Pro Val
 1

<210> SEQ ID NO 25
<211> LENGTH: 21
<212> TYPE: PRT
<213> ORGANISM: Artificial Sequence
<220> FEATURE:
<223> OTHER INFORMATION: Description of Artificial  Sequence:  Amino
      terminal sequence

<400> SEQUENCE: 25

Ile Val Gly Gly Asp Ala Pro Val Gly Lys Tyr Pro Tyr Gln Val Ser
 1               5                  10                  15

Leu Arg Leu Ser Gly
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial  Sequence:  Amino
      terminal sequence

<400> SEQUENCE: 26

Ile Val Gly Gly Glu Pro Ala Pro Gly Gly Ala Tyr Pro Phe Ile Val
 1               5                  10                  15

Ser Leu Gln Val
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial  Sequence:  Amino
      terminal sequence

<400> SEQUENCE: 27

Ile Val Gly Gly Gln Pro Ala Thr Pro Gly Glu Phe Pro His Gln Gly
 1               5                  10                  15

Ser Leu Arg Val
            20

<210> SEQ ID NO 28
<211> LENGTH: 25
<212> TYPE: PRT
<213> ORGANISM: Artificial Sequence
<220> FEATURE:
<223> OTHER INFORMATION: Description of Artificial  Sequence:  Amino
      terminal sequence

<400> SEQUENCE: 28

Ile Val Gly Gly Gln Asp Ala Ala Pro Gly Glu Phe Pro His Gln Gly
 1               5                  10                  15

Ser Leu Arg Leu Arg Gly Ser His Ile
            20                  25

<210> SEQ ID NO 29
<211> LENGTH: 5
<212> TYPE: PRT
<213> ORGANISM: Artificial Sequence
<220> FEATURE:
```

<223> OTHER INFORMATION: Description of Artificial Sequence: Trypsin
      activation peptide sequence

<400> SEQUENCE: 29

Asp Asp Asp Asp Lys
 1               5

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Degenerate
      oligonucleotide probe
<221> NAME/KEY: modified_base
<222> LOCATION: (9)
<223> OTHER INFORMATION: inosine
<221> NAME/KEY: misc_difference
<222> LOCATION: (18)
<223> OTHER INFORMATION: N = A, G, C, or T

<400> SEQUENCE: 30
ccytgatgng graaytcncc                                              20

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Amino
      terminal sequence

<400> SEQUENCE: 31

Ile Val Gly Gly
 1

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Putative
      activation peptide sequence

<400> SEQUENCE: 32

Glu Glu Pro Arg Lys
 1               5

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 33
gagagagaga gagagagaga actagtctct gagttttttt ttttttttttt t          51